(12) United States Patent
Kim et al.

(10) Patent No.: US 10,254,877 B2
(45) Date of Patent: Apr. 9, 2019

(54) TOUCH PANEL APPARATUS FOR MEASURING BIOSIGNALS AND METHOD OF MEASURING BIOSIGNALS BY USING THE SAME

(71) Applicant: SAMSUNG ELECTRONICS CO., LTD., Suwon-si (KR)

(72) Inventors: Sunkwon Kim, Suwon-si (KR); Jaemin Kang, Seoul (KR); Yongjoo Kwon, Yongin-si (KR); Younho Kim, Hwaseong-si (KR); Sangyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 27 days.

(21) Appl. No.: 14/922,586

(22) Filed: Oct. 26, 2015

(65) Prior Publication Data

US 2016/0147367 A1 May 26, 2016

(30) Foreign Application Priority Data

Nov. 21, 2014 (KR) .................. 10-2014-0163816

(51) Int. Cl.
*G06F 3/01* (2006.01)
*A61B 5/053* (2006.01)
(Continued)

(52) U.S. Cl.
CPC .......... *G06F 3/0416* (2013.01); *A61B 5/0404* (2013.01); *A61B 5/04085* (2013.01);
(Continued)

(58) Field of Classification Search
None
See application file for complete search history.

(56) References Cited

U.S. PATENT DOCUMENTS 7,894,888 B2 2/2011 Chan et al.
8,698,760 B2 4/2014 Prendergast et al.
(Continued)

FOREIGN PATENT DOCUMENTS

CN 102004572 A 4/2011
CN 103034364 A 4/2013
(Continued)

OTHER PUBLICATIONS

Yu M. Chi, et al; "Wireless Non-contact EEG/ECG Electrodes for Body Sensor Networks"; International Conference on Body Sensor Networks (BSN); Jun. 7-9, 2010; http://ieeexplore.ieee.org/xpl/articleDetails.jsp?arnumber=5504769&newsearch=true&queryText=Wireless%20Non-contact%20EEG%2FECG%20Electrodes%20for%20Body%20Sensor%20Networks; 5 pgs.
(Continued)

*Primary Examiner* — Alexander Eisen
*Assistant Examiner* — Kebede T Teshome
(74) *Attorney, Agent, or Firm* — Sughrue Mion, PLLC

(57) ABSTRACT

A touch panel apparatus for measuring biosignals and a method of measuring the biosignals by using the touch panel apparatus, are provided. The touch panel apparatus includes a first electrode array configured to detect touch input signals, a second electrode array configured to be coupled to the first electrode array based on driving power, a controller configured to determine an operation mode of the touch panel apparatus as either a manipulation mode configured to manipulate a screen of the touch panel apparatus or a measuring mode configured to measure the biosignals, based on the detected touch input signals, and a mode converter configured to connect the second electrode array to a source of the driving power in response to the controller determining the operation mode as the manipulation mode, and connect the second electrode array to ground in response to
(Continued)

the controller determining the operation mode as the measuring mode.

23 Claims, 31 Drawing Sheets

(51) Int. Cl.
    *G06F 3/041*     (2006.01)
    *G06F 3/044*     (2006.01)
    *A61B 5/0404*     (2006.01)
    *A61B 5/0408*     (2006.01)
    *A61B 5/0428*     (2006.01)
    *A61B 5/0478*     (2006.01)
    *A61B 5/0492*     (2006.01)
    *G06F 3/0488*     (2013.01)

(52) U.S. Cl.
    CPC ........ *A61B 5/04284* (2013.01); *A61B 5/0537* (2013.01); *G06F 3/011* (2013.01); *G06F 3/044* (2013.01); *G06F 3/0412* (2013.01); *G06F 3/04883* (2013.01); *A61B 5/0478* (2013.01); *A61B 5/0492* (2013.01); *G06F 2203/011* (2013.01); *G06F 2203/04112* (2013.01); *G06F 2203/04808* (2013.01)

(56) References Cited

U.S. PATENT DOCUMENTS

| | | | |
|---|---|---|---|
| 9,104,274 | B2 | 8/2015 | Kim et al. |
| 9,372,560 | B2 | 6/2016 | Cho et al. |
| 2008/0246723 | A1* | 10/2008 | Baumbach .......... G06F 3/03547 345/156 |
| 2011/0061949 | A1* | 3/2011 | Krah .................. G06F 3/0418 178/18.06 |
| 2011/0150291 | A1 | 6/2011 | Jung |
| 2012/0249433 | A1 | 10/2012 | Deng et al. |
| 2012/0310071 | A1* | 12/2012 | Nakao .................. A61B 5/0408 600/393 |
| 2013/0088444 | A1 | 4/2013 | Kim et al. |
| 2013/0278555 | A1* | 10/2013 | Cho ........................ G06F 3/041 345/174 |
| 2014/0051941 | A1 | 2/2014 | Messerschmidt |
| 2014/0120876 | A1 | 5/2014 | Shen |
| 2014/0148719 | A1 | 5/2014 | Yang et al. |
| 2015/0185936 | A1* | 7/2015 | Kim ...................... G06F 3/0412 345/174 |
| 2015/0199102 | A1* | 7/2015 | Koh ...................... G06F 3/0488 715/835 |
| 2016/0357327 | A1* | 12/2016 | Chang .................. G06F 3/0418 |

FOREIGN PATENT DOCUMENTS

| | | |
|---|---|---|
| CN | 103376964 A | 10/2013 |
| JP | 4425428 B2 | 3/2010 |
| JP | 2011-101299 A | 5/2011 |
| JP | 2014-94097 A | 5/2014 |
| KR | 10-2010-0044384 A | 4/2010 |
| KR | 20100044384 * | 4/2010 |
| KR | 10-1192932 B1 | 10/2012 |

OTHER PUBLICATIONS

Communication from the European Patent Office dated Mar. 29, 2016 in a counterpart European Application No. 15195068.0.

Communication dated Oct. 25, 2018, from the State Intellectual Property Office of People's Republic of China in counterpart Application No. 201510795195.8.

* cited by examiner

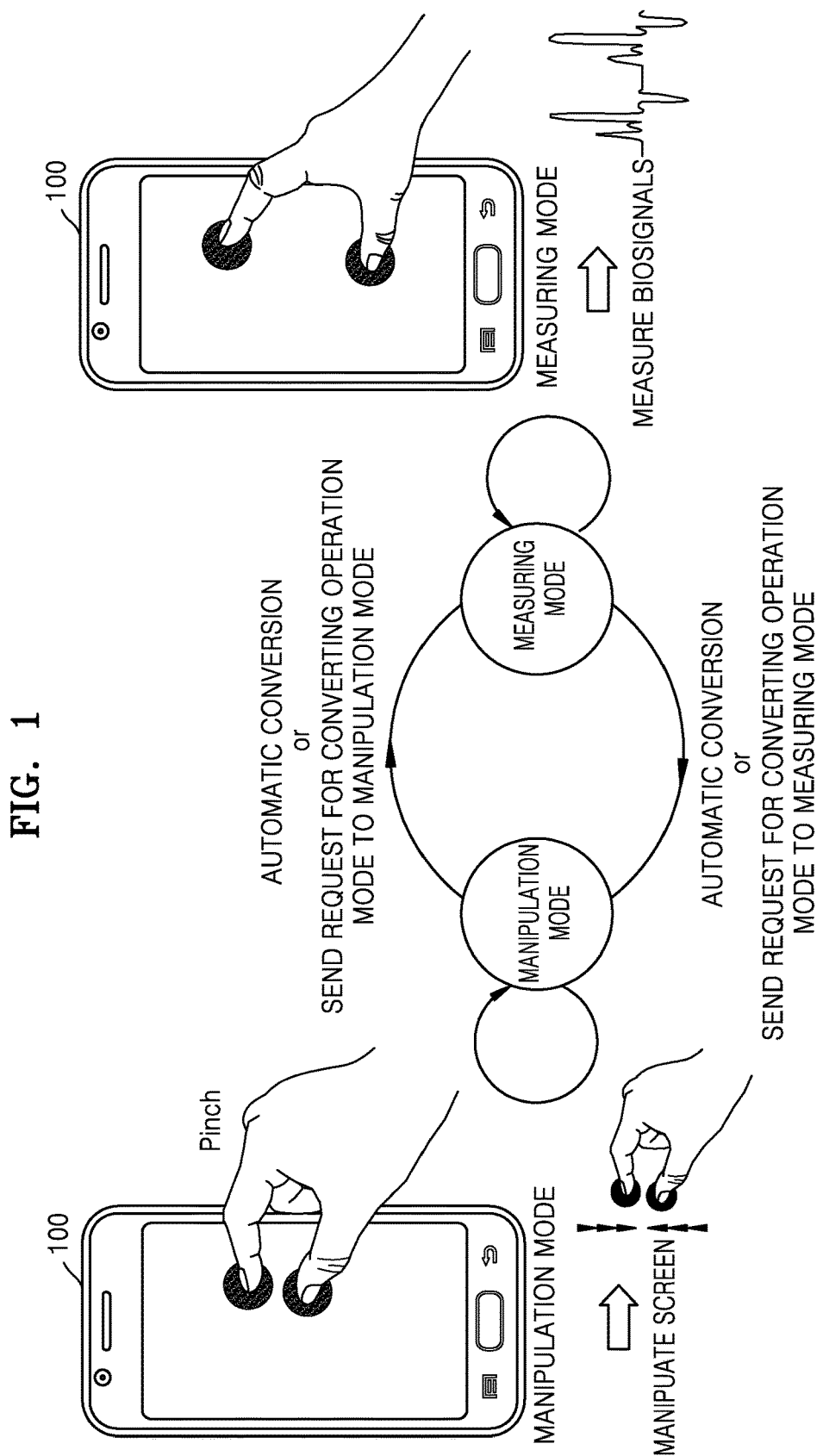

TOUCH PANEL APPARATUS FOR MEASURING BIOSIGNALS AND METHOD OF MEASURING BIOSIGNALS BY USING THE SAME

CROSS-REFERENCE TO RELATED APPLICATION

This application claims priority from Korean Patent Application No. 10-2014-0163816, filed on Nov. 21, 2014, in the Korean Intellectual Property Office, the disclosure of which is incorporated herein in its entirety by reference.

BACKGROUND

1. Field

Apparatuses and methods consistent with exemplary embodiments relate to a touch panel apparatus for measuring biosignals and a method of measuring the biosignals by using the touch panel apparatus.

2. Description of the Related Art

Touch panel technology has been generally applied to mobile devices such as smart phones and wearable devices such as smart watches. The touch panel technology may be variously implemented, but capacitive touch panel technology has been mostly used in personal devices, for example, the mobile devices and wearable devices.

With developments in technology, a user can monitor his or her health by using personal devices such as the mobile devices and wearable devices. Interest in a method of easily measuring biosignals by using the personal devices to check bio information of the user has increased.

SUMMARY

Exemplary embodiments address at least the above problems and/or disadvantages and other disadvantages not described above. Also, one or more exemplary embodiments are not required to overcome the disadvantages described above, and an exemplary embodiment may not overcome any of the problems described above.

One or more exemplary embodiments provide a touch panel apparatus for selectively manipulating a screen thereof or measuring biosignals and a method of measuring the biosignals by using the touch panel apparatus based on touch input signals detected by the touch panel apparatus.

According to an aspect of an exemplary embodiment, a touch panel apparatus for measuring biosignals, includes a first electrode array configured to detect touch input signals, a second electrode array configured to be coupled to the first electrode array based on driving power, and a controller configured to determine an operation mode of the touch panel apparatus as either a manipulation mode configured to manipulate a screen of the touch panel apparatus or a measuring mode configured to measure the biosignals, based on the detected touch input signals. The touch panel apparatus further includes a mode converter configured to connect the second electrode array to a source of the driving power in response to the controller determining the operation mode as the manipulation mode, and connect the second electrode array to ground in response to the controller determining the operation mode as the measuring mode.

The controller may be further configured to combine electrodes included in the first electrode array to form a biosignal electrode configured to measure the biosignals, in response to the controller determining the operation mode as the measuring mode.

The controller may be further configured to adjust a size and a location of the biosignal electrode.

The touch panel apparatus may further include a variable impedance circuit connected to the first electrode array, and the controller may be further configured to adjust an impedance of the variable impedance circuit to adjust an input impedance of the first electrode array in the measuring mode to be larger than an input impedance of the first electrode array in the manipulation mode, in response to the controller determining the operation mode as the measuring mode.

Based on the second electrode array being divided into a first area and a second area, the mode converter may be further configured to connect the first area to the source, and connect the second area to ground, in response to the controller determining the operation mode as the measuring mode.

The controller may be further configured to combine electrodes included in the first electrode array in a location corresponding to the second area to form a biosignal electrode configured to measure the biosignals, in response to the controller determining the operation mode as the measuring mode.

The touch panel apparatus may further include a measurer configured to measure at least one among locations and patterns of the detected touch input signals in response to the controller determining the operation mode as the manipulation mode, and measure sizes of the biosignals based on the detected touch inputs, in response to the controller determining the operation mode as the measuring mode.

The controller may be configured to determine the operation mode as the manipulation mode or the measuring mode, based on changes of locations or patterns of the detected touch input signals.

Based on the locations or patterns of the detected touch input signals being changed, the controller may be configured to determine the operation mode as the manipulation mode.

The controller may be configured to determine the operation mode as the manipulation mode or the measuring mode, based on a touch input signal requesting a conversion of the operation mode.

According to an aspect of another exemplary embodiment, a method of measuring biosignals by using a touch panel apparatus, includes applying driving power to a second electrode array to couple the second electrode array to a first electrode array detecting touch input signals, converting an operation mode of the touch panel apparatus from a manipulation mode configured to manipulate a screen of the touch panel apparatus to a measuring mode configured to measure the biosignals, based on the detected touch input signals, and connecting the second electrode array to ground, and measuring the biosignals based on the detected touch input signals, in response to the converting the operation mode to the measuring mode.

The method may further include combining electrodes included in the first electrode array to form a biosignal electrode measuring the biosignals, in response to the converting the operation mode to the measuring mode, and the measuring may include measuring the biosignals based on touch input signals that are detected by the biosignal electrode.

The method may further include adjusting a size and a location of the biosignal electrode.

The method may further include adjusting an input impedance of the first electrode array in the measuring mode to be larger than an input impedance of the first electrode array in the manipulation mode, in response to the converting the operation mode to the measuring mode, and the measuring may include measuring the biosignals based on the touch input signals detected by the first electrode array having the adjusted input impedance.

The connecting may include, based on the second electrode array being divided into a first area and a second area, connecting the first area to a source of the driving power, and connecting the second area to ground, in response to the converting the operation mode to the measuring mode.

The method may further include combining electrodes included in the first electrode array in a location corresponding to the second area to form a biosignal electrode measuring the biosignals, in response to the converting the operation mode to the measuring mode, and the measuring may include measuring the biosignals based on touch input signals that are detected by the biosignal electrode.

The measuring may include measuring sizes of the biosignals based on the detected touch input signals, in response to the converting the operation mode to measuring mode.

The method may further include converting the operation mode from the measuring mode to the manipulation mode, based on changes of locations or patterns of the detected touch input signals.

The converting may include converting the operation mode based on a touch input signal requesting a conversion of the operation mode.

A non-transitory computer-readable storage medium may store a program including instructions configured to cause a computer to perform the method.

According to an aspect of another exemplary embodiment, a touch panel apparatus includes a first electrode array configured to detect touch input signals, a second electrode array configured to be coupled to the first electrode array based on driving power, and a mode converter configured to connect the second electrode array to a source of the driving power based on the detected touch input signals being changed, and connect the second electrode array to ground based on the detected touch input signals not being changed for a period of time.

The touch panel apparatus may further include a measurer configured to measure at least one among locations and patterns of the detected touch input signals in response to the detected touch input signals being changed, and measure sizes of biosignals based on the detected touch input signals, in response to the detected touch input signals not being changed for the period of time.

The touch panel apparatus may further include a controller configured to activate electrodes among the first electrode array, and deactivate remaining electrodes among the first electrode array, based on the detected touch input signals not being changed for the period of time, and a measurer configured to measure sizes of biosignals based on the touch input signals detected by the activated electrodes.

BRIEF DESCRIPTION OF THE DRAWINGS

The above and/or other aspects will be more apparent by describing exemplary embodiments with reference to the accompanying drawings, in which:

FIG. 1 is a view for explaining a touch panel apparatus having multiple operation modes, according to an exemplary embodiment;

DETAILED DESCRIPTION OF THE EXEMPLARY EMBODIMENTS

Figure 2A:
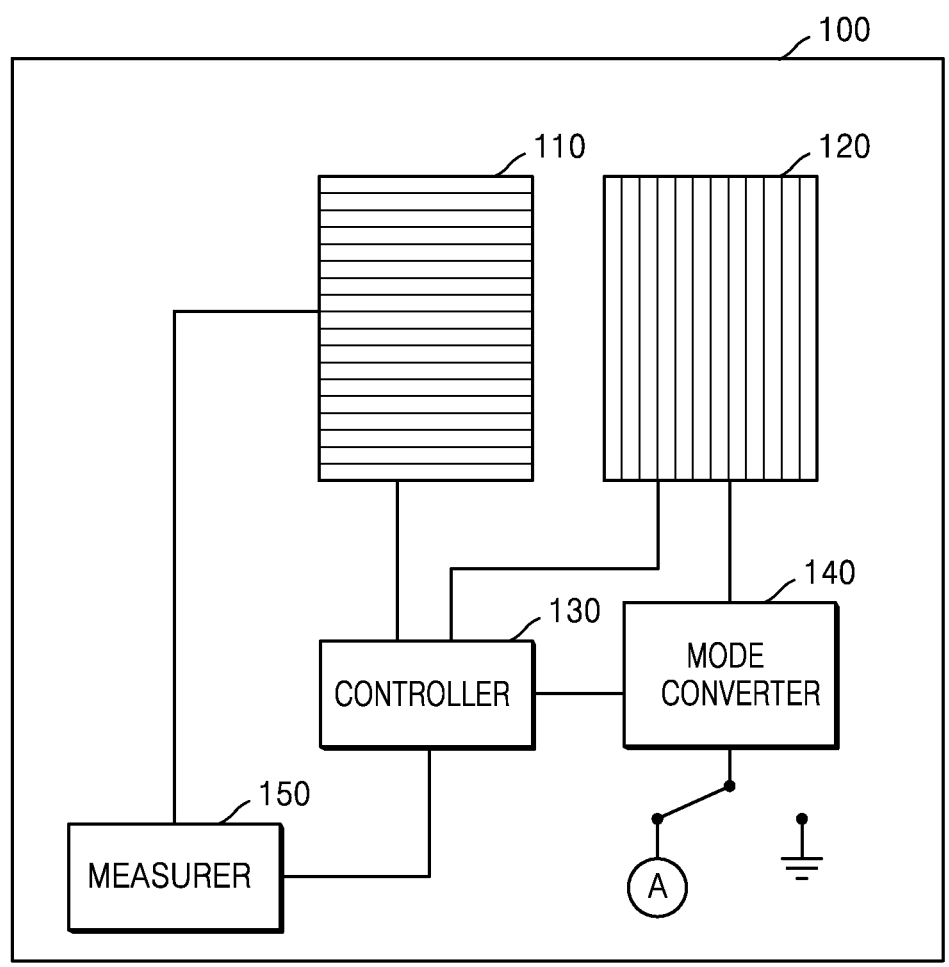
FIGS. 2A and 2B are block diagrams of structures and operations of a touch panel apparatus when operation modes of the touch panel apparatus are a manipulation mode and a measuring mode, according to an exemplary embodiment.

Exemplary embodiments are described in greater detail with reference to the accompanying drawings.

Exemplary embodiments of the present disclosure may be diversely modified. Accordingly, the exemplary embodiments are illustrated in the drawings and are described in detail in the detailed description. However, it is to be understood that the present disclosure is not limited to a specific exemplary embodiment, but includes all modifications, equivalents, and substitutions without departing from the scope and spirit of the present disclosure. Also, well-known functions or constructions may not be described in detail because they would obscure the disclosure with unnecessary detail.

In the following description, the same drawing reference numerals are used for the same elements even in different drawings. The matters defined in the description, such as detailed construction and elements, are provided to assist in a comprehensive understanding of the exemplary embodiments. Thus, it is apparent that the exemplary embodiments can be carried out without those specifically defined matters.

Hereinafter, it is understood that expressions such as "at least one of," when preceding a list of elements, modify the entire list of elements and do not modify the individual elements of the list.

It will be further understood that the terms "comprises" and/or "comprising" used herein specify the presence of stated features or components, but do not preclude the presence or addition of one or more other features or components.

While such terms as "first", "second", etc., may be used to describe various components, such components may not be limited to the above terms. The above terms are used to distinguish one component from another.

In addition, the terms such as "unit," "-er (-or)," and "module" described in the specification refer to an element for performing at least one function or operation, and may be implemented in hardware, software, or the combination of hardware and software.

One or more exemplary embodiments relate to a touch panel apparatus for measuring biosignals and a method of measuring the biosignals by using the touch panel apparatus.

Biosignals are any signals detected from a human body and include bioelectric signals, bio-impedance signals, or the like. The bioelectric signals may be in a current or voltage form, the current or voltage being generated by muscle cells or neurons. For example, electrocardiogram (ECG) signals, electromyogram (EMG) signals, electroencephalogram (EEG) signals, etc. are the bioelectric signals. The bio-impedance signals are based on a voltage drop occurring due to an impedance of tissues, which is generated when a predetermined level of current flows in the tissues. The bio-impedance signals may include information concerning body composition, blood volume, blood distribution, or the like. For example, body fat may be measured by using the bio-impedance signals.

In the present specification, the touch panel apparatus is configured to receive input signals when a user touches a screen thereof with a body part of the user, and refers to all types of devices, for example, a touch screen, a touch pad, etc., which include a touch panel. The touch panel apparatus may be a mobile terminal such as a smart phone or a wearable device such as smart glasses or a smart watch, but is not limited thereto. When a body part of the user is placed in contact with texts, images, etc., displayed by a display having a touch panel, the touch panel apparatus identifies what is selected by the user according to which portion of the display is in contact with the body part of the user, processes a command corresponding to the selected portion by using a processor, and then displays, on a screen, information that the user wants. The touch panel apparatus may be variously implemented, and may be a capacitive touch panel apparatus that detects a capacitance change.

FIG. 1 is a view for explaining a touch panel apparatus 100 having multiple operation modes, according to an exemplary embodiment.

Referring to FIG. 1, the touch panel apparatus 100 has two operation modes, that is, a manipulation mode and a measuring mode. The manipulation mode is configured to manipulate a screen of the touch panel apparatus 100 based on touch input signals, and the measuring mode is configured to measure biosignals based on the touch input signals. The touch panel apparatus 100 may have at least two operation modes including the manipulation mode and the measuring mode.

The touch panel apparatus 100 may automatically convert the operation mode based on a user request for converting the operation mode or detected touch input signals. For example, the touch panel apparatus 100 may convert the operation mode from the manipulation mode to the measuring mode or from the measuring mode to the manipulation mode based on the detected touch input signals.

When the touch panel apparatus 100 is in the manipulation mode, the touch panel apparatus 100 may process and display a screen based on touch input signals input by the user. For example, as shown on a left side of FIG. 1, when the user uses two fingers to perform pinching on the screen of the touch panel apparatus 100, the touch panel apparatus 100 detects touch input signals corresponding to the pinching and may increase or decrease a size of the screen.

In the measuring mode, the touch panel apparatus 100 may measure biosignals based on touch input signals which are input onto the screen by the user. For example, as shown on a right side of FIG. 1, when the user touches the screen with a body part and does not move for a predetermined time, the touch panel apparatus 100 detects touch input signals corresponding to a change of an electric field, which is caused by the body part placed in contact with the screen, and may measure the biosignals.

Hereinafter, the touch panel apparatus for manipulating a screen of the touch panel apparatus 100 and measuring the biosignals based on the touch input signals detected in the touch panel apparatus 100, and the method of measuring the biosignals by using the touch panel apparatus, will be described.

Figure 2B:
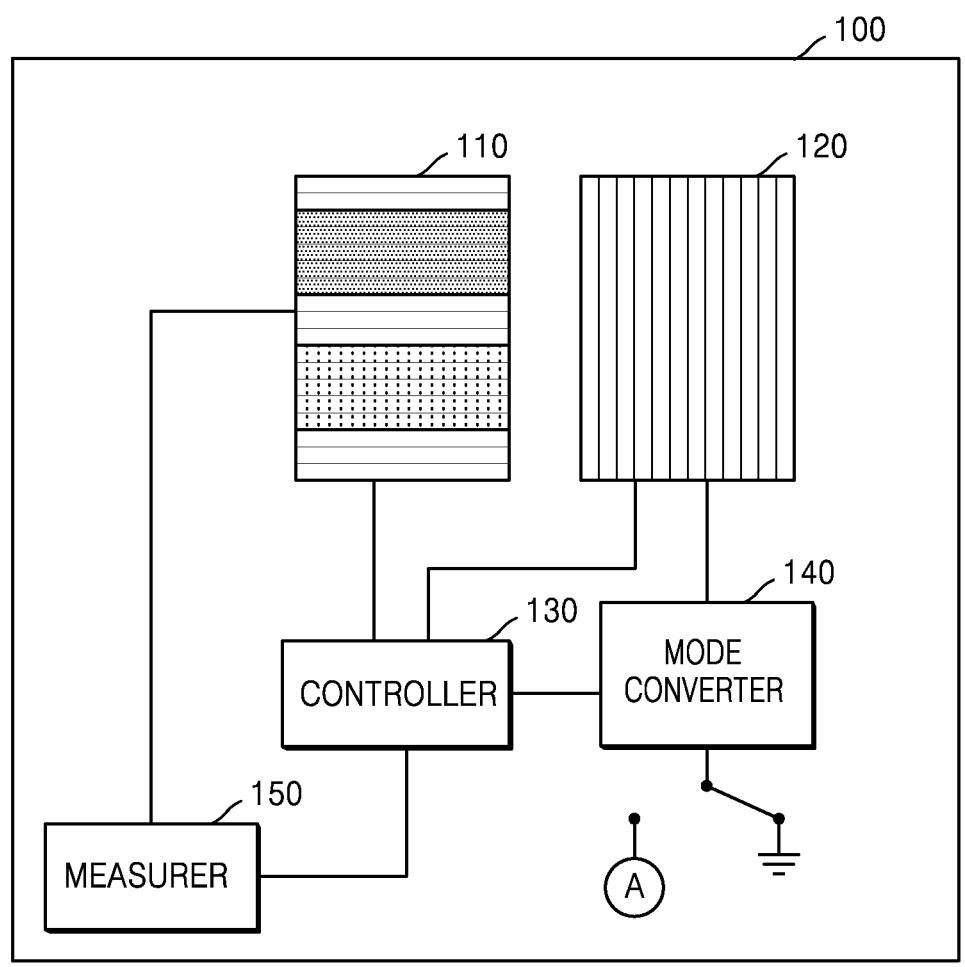

FIGS. 2A and 2B are block diagrams of structures and operations of the touch panel apparatus 100 when operation modes of the touch panel apparatus 100 are a manipulation mode and a measuring mode, according to an exemplary embodiment. It may be understood by one of ordinary skill in the art that general-purpose components, other than the components illustrated in FIGS. 2A and 2B, may be further included.

Referring to FIGS. 2A and 2B, the touch panel apparatus 100 includes a first electrode array 110, a second electrode array 120, a controller 130, a mode converter 140, and a measurer. Unlike the illustrations of FIGS. 2A and 2B, the measurer 150 may be included in the controller 130.

The first electrode array 110 may include reception electrodes capable of detecting touch input signals of the user. Each of the reception electrodes forming the first electrode array 110 may be a transparent electrode formed of indium tin oxide (ITO) layers.

The second electrode array 120 may include driving electrodes field-coupled to the first electrode array 110 according to driving power. Each of the driving electrodes forming the second electrode array 120 may be a transparent electrode formed of ITO layers.

Depending on implementation methods of a touch panel, at least one of a substrate, an insulating layer, and a film may be included between the first electrode array 110 and the second electrode array 120. In consideration of an internal space of the touch panel apparatus 100, the first electrode array 110 may be disposed in an upper level to the second electrode array 120.

The reception electrodes included in the first electrode array 110 may be arranged in a first axial direction. The driving electrodes included in the second electrode array 120 may be arranged in a second axial direction. When the first electrode array 110 overlaps with the second electrode array 120 on a plane, the first axial direction in which the reception electrodes included in the first electrode array 110 are arranged may be perpendicular to the second axial direction in which the driving electrodes included in the second electrode array 120 are arranged. Hereinafter, the first axial direction in which the reception electrodes included in the first electrode array 110 are arranged will be referred to as a row direction, and the second axial direction in which the driving electrodes included in the second electrode array 120 are arranged will be referred to as a column direction.

The first electrode array 110 and the second electrode array 120 may be field-coupled to each other according to the driving power applied to the second electrode array 120. If a constant level of the driving power is continuously applied to the second electrode array 120, field coupling may be maintained. In this case, when the first electrode array 110 comes in contact with a body part of the user, the field coupling may change. Accordingly, a current flowing through the electrodes included in the first electrode array 110 may change. The touch panel apparatus 100 may detect the touch input signals of the user based on a change of the current flowing through the electrodes included in the first electrode array 110.

The controller 130 may control the touch panel apparatus 100. In other words, the controller 130 may control operations of the first electrode array 110, the second electrode array 120, the mode converter 140, and the measurer 150.

The controller 130 may respectively control operations of electrodes included in the first electrode array 110 and the second electrode array 120. For example, the controller 130 activates an electrode among the electrodes included in the first electrode array 110 and may determine which touch input signal is to be detected. Also, the controller 130 may determine which electrode among the electrodes included in the second electrode array 120 is to receive the driving power.

Based on the detected touch input signals, the controller 130 may determine an operation mode of the touch panel apparatus 100 as either a manipulation mode configured to manipulate a screen of the touch panel apparatus 100 or a measuring mode configured to measure the biosignals. For example, the controller 130 may automatically determine the operation mode of the touch panel apparatus 100 according to whether locations or patterns of the detected touch input signals are changed. In other words, the controller 130 determines the operation mode of the touch panel apparatus 100 as the manipulation mode if the locations or patterns of the detected touch input signals are changed, and if the locations or patterns of the detected touch input signals are not changed, the controller 130 determines the operation mode of the touch panel apparatus 100 as the measuring mode. As another example, the controller 130 may determine the operation mode of the touch panel apparatus 100 based on a touch input signal requesting a mode conversion. The operation mode of the touch panel apparatus 100 may be converted when the user presses a mechanical push button or a display-type button displayed on the screen of the touch panel apparatus 100 to perform the mode conversion.

The mode converter 140 may maintain a current operation mode or convert the current operation mode to another operation mode, according to the operation mode determined by the controller 130. The mode converter 140 may connect the second electrode array 120 to the driving power source in the manipulation mode and may connect the second electrode array 120 to ground in the measuring mode.

As shown in FIG. 2A, when the touch panel apparatus 100 is in the manipulation mode, the mode converter 140 may connect the second electrode array 120 to the power source supplying the driving power. When the second electrode array 120 is connected to the driving power source, the first electrode array 110 and the second electrode array 120 are field-coupled to each other, and the touch panel apparatus 100 may detect the touch input signals generated according to a change of the electric field. When the driving power is applied to the second electrode array 120, the controller 130 sequentially operates row electrodes included in the first electrode array 110 for each column electrode included in the second electrode array 120, and thus, the controller 130 may detect whether the touch input signals are input to a screen disposed above the first electrode array 110.

On the contrary, as shown in FIG. 2B, when the touch panel apparatus 100 is in the measuring mode, the mode converter 140 may connect the second electrode array 120 to ground. When the second electrode array 120 is connected to ground, in other words, when the driving power is not applied to the second electrode array 120, the second electrode array 120 may not be field-coupled to the first electrode array 110. Instead, when the second electrode array 120 is in a grounded state, the second electrode array 120 may shield the first electrode array 110. In detail, because the first electrode array 110 is disposed in an upper level to the second electrode array 120 in consideration of an internal space of the touch panel apparatus 100, the second electrode array 120 may shield the first electrode array 110 when the second electrode array 120 is connected to ground. In other words, when an entire portion of the second electrode array 120 disposed below the first electrode array 110 is connected to ground, the second electrode array 120 may perform shielding such as blocking noise, etc., which penetrate from a lower portion of the second electrode array 120 to the first electrode array 110. Accordingly, the first electrode array 110 may detect minute touch input signals having a small amplitude without using a change of the field coupling, wherein the change is made according to the driving power.

The measurer 150 may measure the detected touch input signals. The measurer 150 may measure at least one of locations and patterns of the detected touch input signals in the manipulation mode. The measurer 150 may measure sizes of the biosignals in the measuring mode. Also, the measurer 150 may measure cycles of the biosignals and the number of times that the biosignals are detected in the measuring mode.

Figure 3A:
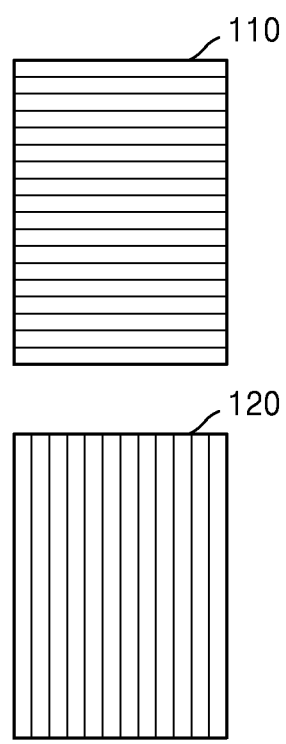
FIGS. 3A and 3B are views for explaining operations of a first electrode array and a second electrode array when operation modes of a touch panel apparatus are a manipulation mode and a measuring mode, according to an exemplary embodiment.
Figure 3B:
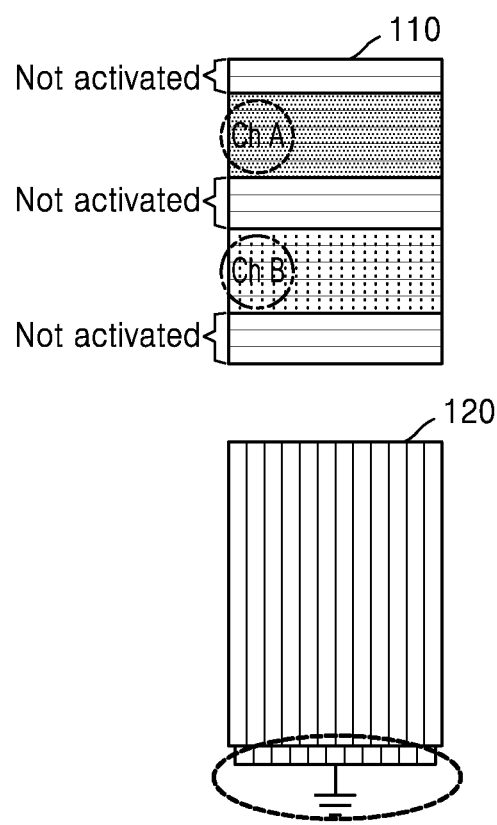

FIGS. 3A and 3B are views for explaining operations of the first electrode array 110 and the second electrode array 120 when operation modes of the touch panel apparatus 100 are a manipulation mode and a measuring mode, according to an exemplary embodiment.

FIG. 3A shows the first electrode array 110 and the second electrode array 120 when the touch panel apparatus 100 is in the manipulation mode. The first electrode array 110 is on the top portion of FIG. 3A, and the second electrode array 120 is on the bottom portion of FIG. 3A. The electrodes included in the first electrode array 110 are arranged in a row direction, and the electrodes included in the second electrode array 120 are arranged in a column direction.

In the manipulation mode, the touch panel apparatus 100 applies the driving power to a first column electrode of the second electrode array 120, and then may detect the touch input signals by operating from a first row electrode to an $N^{th}$ row electrode of the first electrode array 110 (where N is a natural number greater than 1). As described above, the touch panel apparatus 100 sequentially applies the driving power from the first column electrode to an Mth electrode (where M is a natural number greater than 1) of the second electrode array 120, and may detect whether there are the touch input signals input onto an entire screen of the touch panel apparatus 100 by operating from the first row electrode to the $N^{th}$ row electrode of the first electrode array 110.

FIG. 3B shows the first electrode array 110 and the second electrode array 120 when the touch panel apparatus 100 is in the measuring mode. The first electrode array 110 is on the top portion of FIG. 3B, and the second electrode array 120 is on the bottom portion of FIG. 3B. Electrodes included in the first electrode array 110 are arranged in the row direction, and electrodes included in the second electrode array 120 are arranged in the column direction.

In the measuring mode, the touch panel apparatus 100 connects all electrodes included in the second electrode array 120 to ground, and thus, the second electrode array 120 may perform shielding for the first electrode array 110, for example, blocking noise generated in the touch panel apparatus 100. Accordingly, the first electrode array 110 may detect touch input signals having a small amplitude such as biosignals generated from some body parts of the user.

In the measuring mode, the controller 130 of the touch panel apparatus 100 combines the electrodes included in the first electrode array 110 to form a biosignal electrode measuring the biosignals. Referring to FIG. 3B, the controller 130 of the touch panel apparatus 100 simultaneously activates some of the electrodes included in the first electrode array 110 to form two biosignal electrodes. The formed biosignal electrodes may be channels (e.g., Ch A and Ch B) via which the biosignals generated from the body parts of the user are transmitted.

Figure 4A:
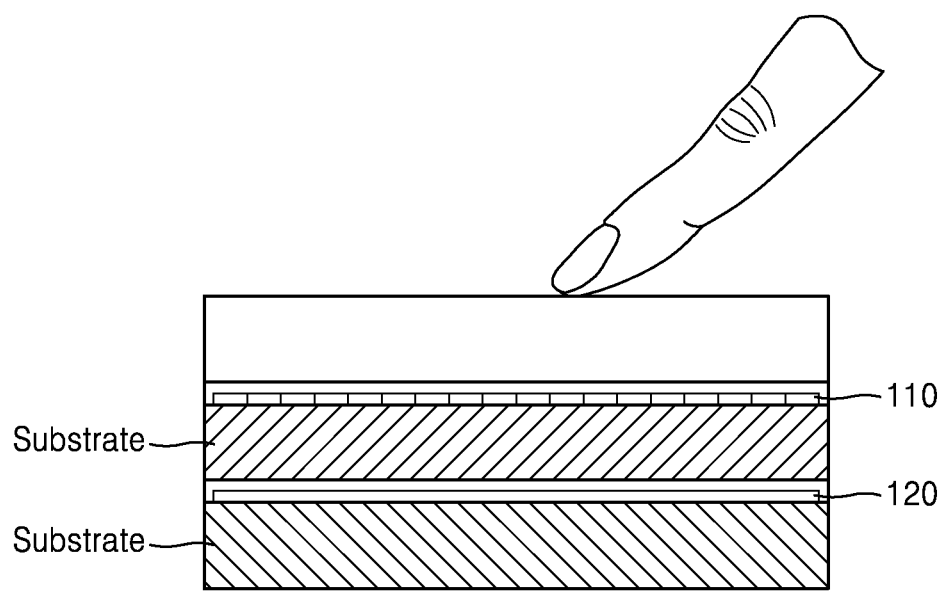
FIGS. 4A and 4B are views for explaining a method of detecting touch input signals when operation modes of a touch panel apparatus are a manipulation mode and a measuring mode, according to an exemplary embodiment.
Figure 4B:
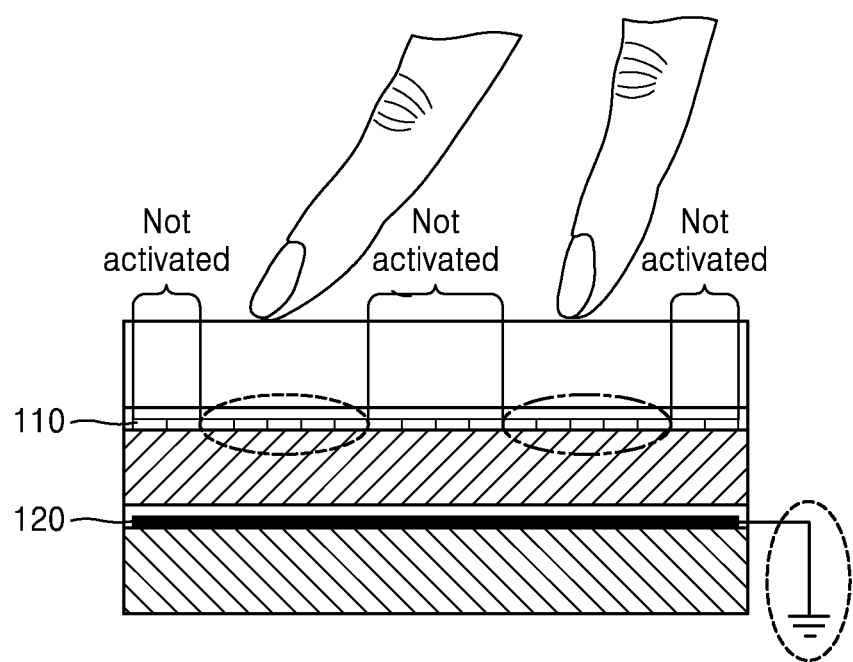

FIGS. 4A and 4B are views for explaining a method of detecting touch input signals when operation modes of the touch panel apparatus 100 are a manipulation mode and a measuring mode, according to an exemplary embodiment. FIGS. 4A and 4B respectively show cross-sections of a touch panel in which ITO layers deposited on two substrates are respectively implemented as the first electrode array 110 and the second electrode array 120.

FIG. 4A shows a stack structure in which the first electrode array 110 and the second electrode array 120 are respectively formed on substrates when the touch panel apparatus 100 is in the manipulation mode. An upper layer of the touch panel apparatus 100 is the first electrode array 110, and a lower layer of the touch panel apparatus 100 is the second electrode array 120. When the touch panel apparatus 100 is in the manipulation mode, the driving power is applied to the second electrode array 120 that is the lower layer, and thus, the second electrode array 120 is field-coupled to the first electrode array 110. As shown in FIG. 4A, when the user touches the screen of the touch panel apparatus 100 with a fingertip, an electric field between the first electrode array 110 and the second electrode array 120 is changed, and thus, a current flowing through the first electrode array 110 changes. Therefore, the touch panel apparatus 100 may detect the touch input signals.

FIG. 4B shows a stack structure in which the first electrode array 110 and the second electrode array 120 are respectively formed on substrates when the touch panel apparatus 100 is in the measuring mode. An upper layer of the touch panel apparatus 100 is the first electrode array 110, and a lower layer of the touch panel apparatus 100 is the second electrode array 120. When the touch panel apparatus 100 is in the measuring mode, the second electrode array 120 that is the lower layer is connected to ground and thus is in a grounded state. As shown in FIG. 4B, the controller 130 of the touch panel apparatus 100 activates some of the electrodes included in the first electrode array 110 to form biosignal electrodes. When a body part of the user comes in contact with the screen of the touch panel apparatus 100, the biosignal electrodes become channels for transmitting the biosignals, and the biosignals may be measured. In this case, the grounded second electrode array 120 may perform shielding such as blocking various noise generated in a lower portion of the second electrode array 120 of the touch panel apparatus 100.

FIG. 4B shows that the electrodes included in the first electrode array 110 are combined to form two separate biosignal electrodes. However, other exemplary embodiments are not limited thereto.

Figure 5A:
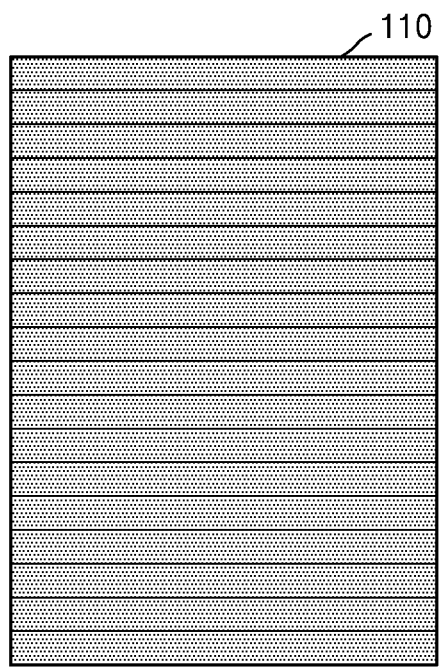
FIGS. 5A, 5B, and 5C are views for explaining various types of a biosignal electrode formed on a first electrode array when a touch panel apparatus is in a measuring mode, according to an exemplary embodiment.
Figure 5B:
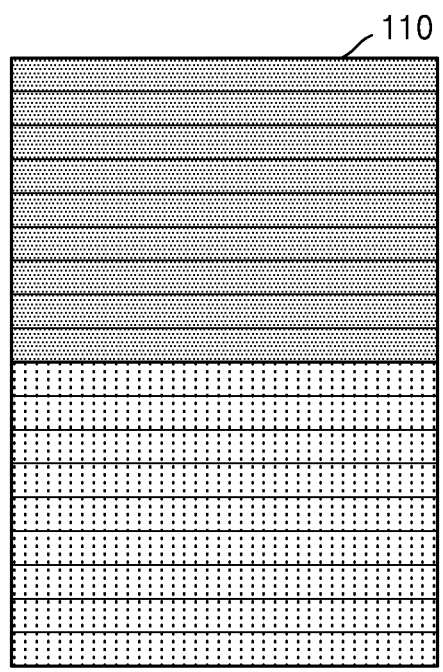
Figure 5C:
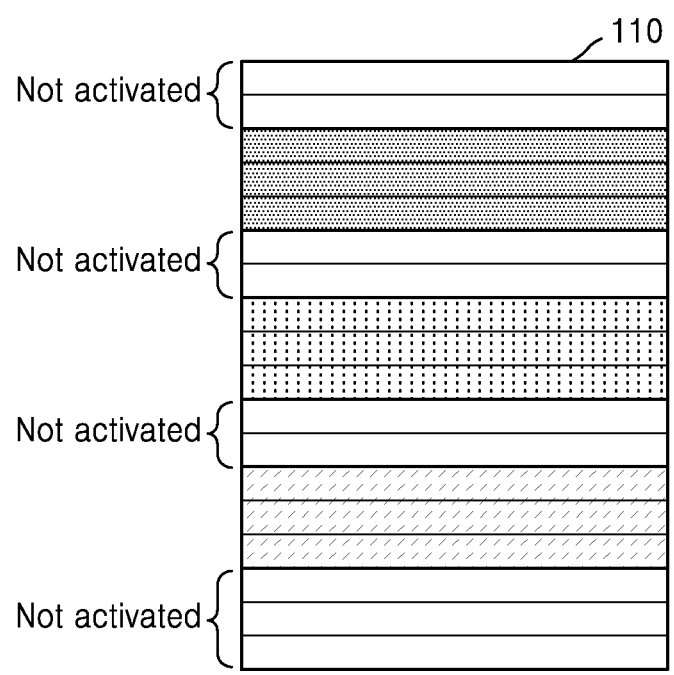

FIGS. 5A, 5B, and 5C are views for explaining various types of a biosignal electrode formed on the first electrode array 110 when the touch panel apparatus 100 is in a measuring mode, according to an exemplary embodiment.

In the measuring mode, the controller 130 of the touch panel apparatus 100 combines the electrodes included in the first electrode array 110 to form biosignal electrodes measuring the biosignals. The controller 130 of the touch panel apparatus 100 may adjust sizes and locations of the biosignal electrodes.

FIG. 5A shows when all electrodes included in the first electrode array 110 are activated, and one biosignal electrode having the largest detection area is formed when the touch panel apparatus 100 is in the measuring mode.

FIG. 5B shows when all electrodes included in the first electrode array 110 are activated, and two biosignal electrodes are formed by dividing the first electrode array 110 into two sections when the touch panel apparatus 100 is in the measuring mode.

FIG. 5C shows when some of the electrodes included in the first electrode array 110 are activated, and three biosignal electrodes are formed by being separated from each other by non-activated electrodes.

When the touch panel apparatus 100 is in the measuring mode, shapes of the biosignal electrodes formed in the first electrode array 110 are not limited thereto.

The touch panel apparatus 100 according to the above exemplary embodiments may measure bioelectric signals such as ECG signals. A capacitive ECG sensor includes planar electrodes, and if the biosignal electrodes, which are formed when the touch panel apparatus 100 is in the measuring mode, are used, the capacitive ECG sensor may measure the bioelectric signals such as ECG signals. Distribution of the biosignal electrodes, which are formed when the touch panel apparatus 100 is in the measuring mode, may differ according to activation or inactivation of each electrode included in the first electrode array 110. In other words, distribution of channels for checking the bioelectric signals such as ECG signals may differ according to the activation or inactivation of each electrode included in the first electrode array 110.

Figure 6A:
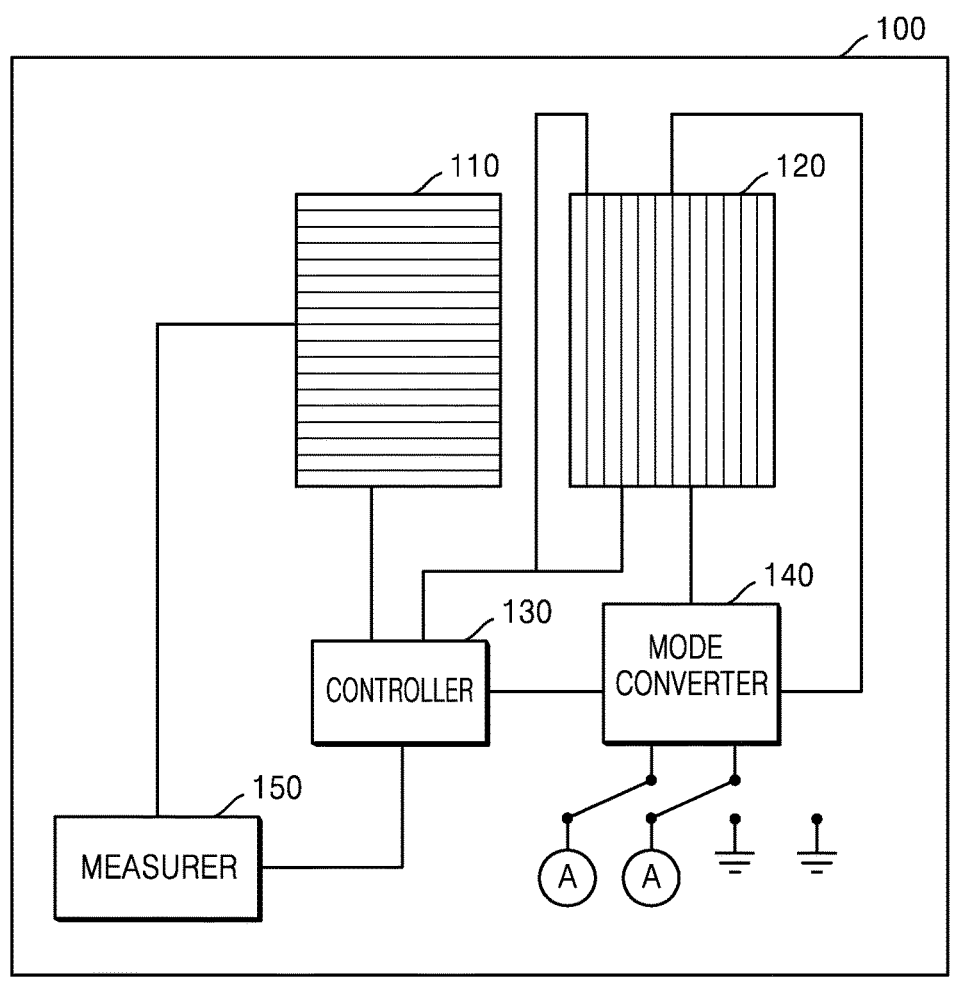
FIGS. 6A and 6B are block diagrams of structures and operations of a touch panel apparatus when operation modes of the touch panel apparatus are a manipulation mode and a measuring mode, according to another exemplary embodiment.
Figure 6B:
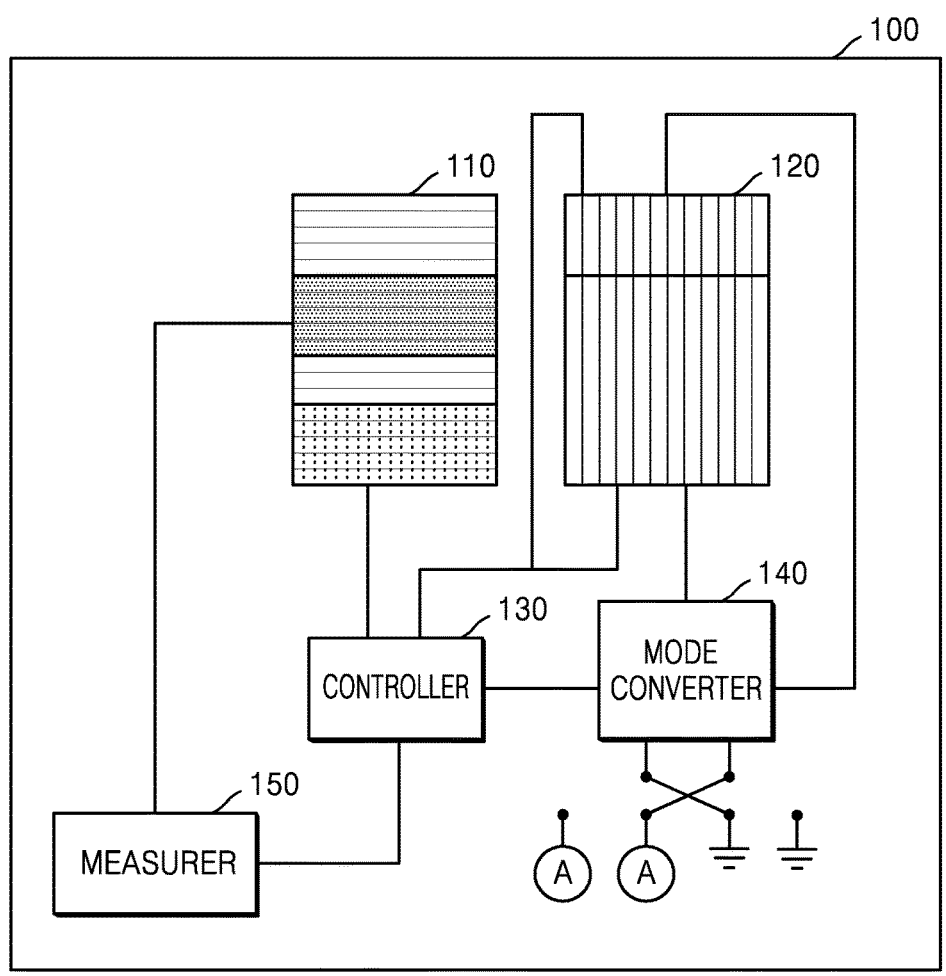

FIGS. 6A and 6B are block diagrams of structures and operations of the touch panel apparatus 100 when operation modes of the touch panel apparatus 100 are a manipulation mode and a measuring mode, according to another exemplary embodiment. It may be understood by one of ordinary skill in the art that general-purpose components, other than the components illustrated in FIGS. 6A and 6B, may be further included.

Referring to FIGS. 6A and 6B, the touch panel apparatus 100 includes the first electrode array 110, the second electrode array 120, the controller 130, the mode converter 140, and the measurer 150. Unlike the illustrations of FIGS. 2A and 2B, FIGS. 6A and 6B show that the second electrode array 120 is divided into two areas. Descriptions that have been already provided with reference to FIGS. 2A and 2B will be omitted.

The first electrode array 110 may include reception electrodes capable of detecting touch input signals of the user. The second electrode array 120 may include driving electrodes which are field-coupled to the first electrode array 110 according to driving power. Electrodes for forming the first electrode array 110 and the second electrode array 120 may respectively be transparent electrodes formed of ITO layers.

As shown in FIGS. 6A and 6B, the second electrode array 120 is divided into two areas. For example, the second electrode array 120 may be divided into a first area and a second area.

Because the second electrode array 120 is divided into the first area and the second area, the first area and the second area of the second electrode array 120 may be independently controlled. For example, electrodes corresponding to the first area of the second electrode array 120 and those corresponding to the second area of the second electrode array 120 may separately operate. Also, the driving power is applied to the electrodes corresponding to the first area of the second electrode array 120, and the electrodes corresponding to the second area of the second electrode array 120 may be connected to ground.

According to types of the biosignals to be measured by the touch panel apparatus 100, a method of measuring the biosignals may be different. For example, when a portion of the second electrode array 120 needs the driving power to be applied thereto when the biosignals are to be measured, the second electrode array 120 is divided into at least two areas, and the biosignals may be measured by applying the driving power to any one of the at least two areas.

When the touch panel apparatus 100 is in the measuring mode, the driving power is applied to the first area of the second electrode array 120, and the second area is connected to ground. The first area may be field-coupled to the first electrode array 110, and the second area may shield the first electrode array 110. In this case, the controller 130 of the touch panel apparatus 100 combines the electrodes corresponding to the second area connected to ground among the electrodes included in the first electrode array 110 to form biosignal electrodes in locations corresponding to the second area to accurately measure the biosignals.

As shown in FIG. 6A, when the touch panel apparatus 100 is in the manipulation mode, the touch input signals may be detected from an entire screen of the touch panel apparatus 100 by applying the driving power to both the first area and the second area of the second electrode array 120.

As shown in FIG. 6B, when the touch panel apparatus 100 is in the measuring mode, the driving power is applied to the first area of the second electrode array 120, and the second area of the second electrode array 120 is connected to ground to measure the biosignals.

Figure 7A:
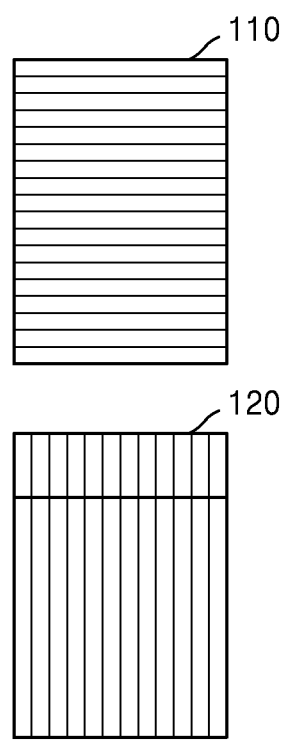
FIGS. 7A and 7B are views for explaining operations of a first electrode array and a second electrode array when operation modes of a touch panel apparatus are a manipulation mode and a measuring mode, according to another exemplary embodiment.
Figure 7B:
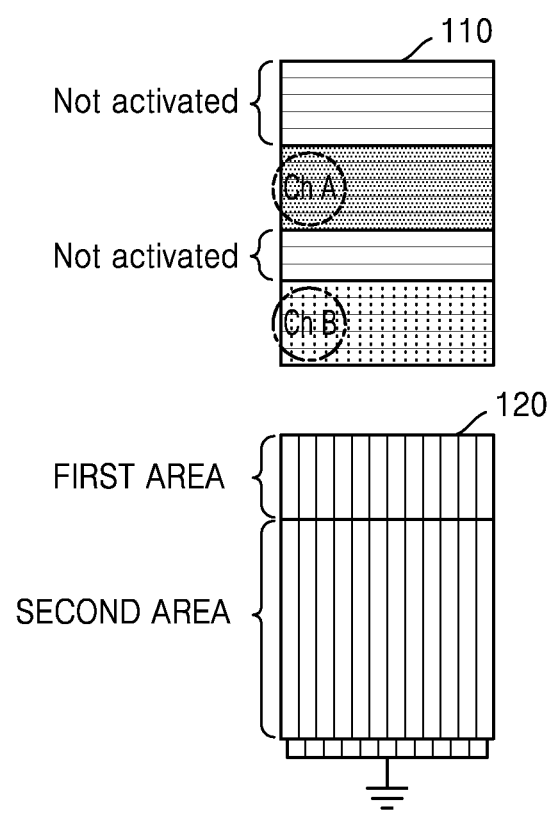

FIGS. 7A and 7B are views for explaining operations of the first electrode array 110 and the second electrode array 120 when operation modes of the touch panel apparatus 100 are a manipulation mode and a measuring mode, according to another exemplary embodiment.

FIG. 7A shows the first electrode array 110 and the second electrode array 120 when the touch panel apparatus 100 is in the manipulation mode. The first electrode array 110 is on the top portion of FIG. 7A, and the second electrode array 120 is on the bottom portion of FIG. 7A. FIG. 7B shows the first electrode array 110 and the second electrode array 120 when the touch panel apparatus 100 is in the measuring mode. The first electrode array 110 is on the top portion of FIG. 7B, and the second electrode array 120 is on the bottom portion of FIG. 7B.

When the touch panel apparatus 100 is in the measuring mode, electrodes corresponding to the second area among the electrodes included in the second electrode array 120 may be connected to ground. The second area of the second electrode array 120 connected to ground may perform shielding, for example, blocking various noise generated inside the touch panel apparatus 100. Accordingly, the first electrode array 110 may detect touch input signals having a small amplitude generated from body parts of the user.

The controller 130 of the touch panel apparatus 100 combines the electrodes included in the first electrode array 110 to form biosignal electrodes measuring the biosignals when the touch panel apparatus 100 is in the measuring mode. Referring to FIG. 7B, the controller 130 of the touch panel apparatus 100 simultaneously activates some of the electrodes included in the first electrode array 110 to form two biosignal electrodes. Also, referring to FIG. 7B, the controller 130 of the touch panel apparatus 100 forms the biosignal electrodes in an area of the first electrode array 110 corresponding to the second area of the second electrode array 120. The biosignal electrodes may be channels via which the biosignals are transmitted to the body parts of the user. Also, referring to FIG. 7B, the electrodes of the first electrode array 110 that are on an area corresponding to the first area of the second electrode array 120 may remain non-activated.

Figure 8A:
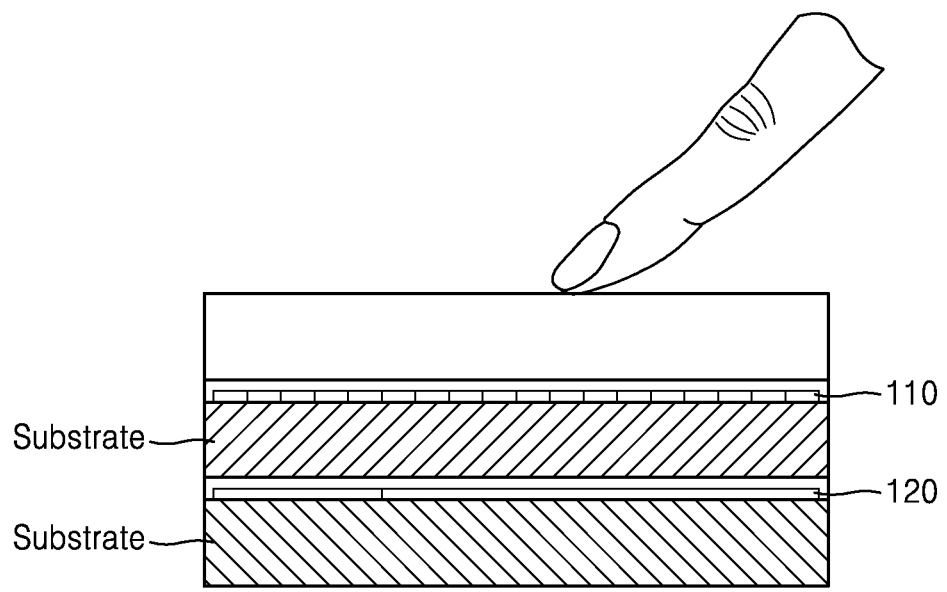
FIGS. 8A and 8B are views for explaining a method of detecting touch input signals when operation modes of a touch panel apparatus are a manipulation mode and a measuring mode, according to another exemplary embodiment.
Figure 8B:
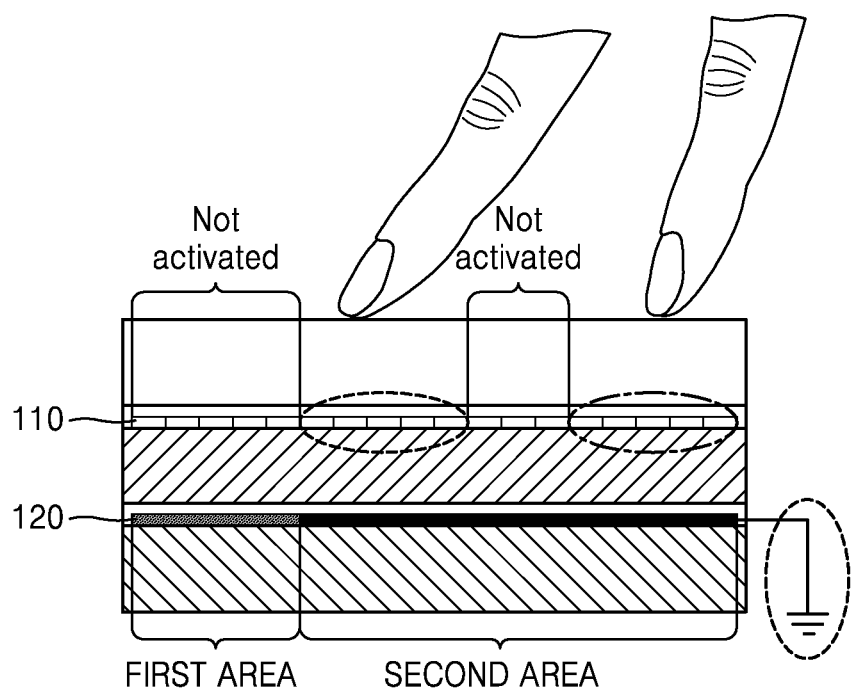

FIGS. 8A and 8B are views for explaining a method of detecting touch input signals when operation modes of the touch panel apparatus 100 are a manipulation mode and a measuring mode, according to another exemplary embodiment.

FIG. 8A shows a stack structure in which the first electrode array 110 and the second electrode array 120 are respectively formed on substrates when the touch panel apparatus 100 is in the manipulation mode. The first electrode array 110 is an upper layer of the touch panel apparatus 100, and the second electrode array 120 is a lower layer of the touch panel apparatus 100. When the touch panel apparatus 100 is in the manipulation mode, the driving voltage is applied to the first area and the second area of the second electrode array 120, and thus, the second electrode array 120 is field-coupled to the first electrode array 110. As shown in FIG. 8A, when the user touches the screen of the touch panel apparatus 100 with a fingertip, the electric field between the first electrode array 110 and the second electrode array 120 changes, and a current flowing through the first electrode array 110 changes. Therefore, the touch input signals may be detected.

FIG. 8B shows a stack structure in which the first electrode array 110 and the second electrode array 120 are respectively formed on the substrates when the touch panel apparatus 100 is in the measuring mode. The first electrode array 110 is an upper layer of the touch panel apparatus 100, and the second electrode array 120 is a lower layer of the touch panel apparatus 100. As shown in FIG. 8B, the second electrode array 120 that is the lower layer may be divided into the first area and the second area. When the touch panel apparatus 100 is in the measuring mode, the second area of the second electrode array 120 is connected to ground and thus is in a grounded state. As shown in FIG. 8B, the controller 130 of the touch panel apparatus 100 activates some of the electrodes included in the first electrode array 110 to form biosignal electrodes. As shown in FIG. 8B, the controller 130 of the touch panel apparatus 100 may form the biosignal electrodes by using some electrodes of the first electrode array 110 that are in a location corresponding to the second area of the second electrode array 120. When a body part of the user comes in contact with the screen of the touch panel apparatus 100, the biosignal electrodes become channels for transmitting the biosignals, and thus, the biosignals may be measured. In this case, the second area of the grounded second electrode array 120 may perform shielding such as blocking noise generated inside the touch panel apparatus 100 from a lower portion of the second electrode array 120.

FIG. 8B shows that the electrodes included in the first electrode array 110 are combined to form two separate biosignal electrodes. However, other exemplary embodiments are not limited thereto.

Figure 9A:
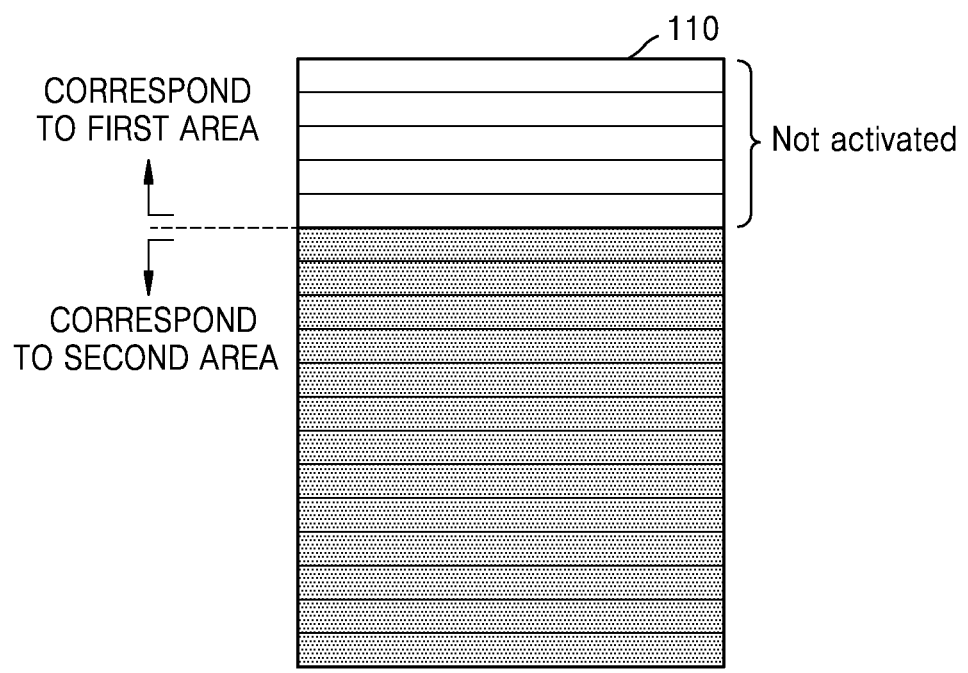
FIGS. 9A, 9B, and 9C are views for explaining various types of biosignal electrodes formed on a first electrode array when a touch panel apparatus is in a measuring mode, according to another exemplary embodiment.
Figure 9B:
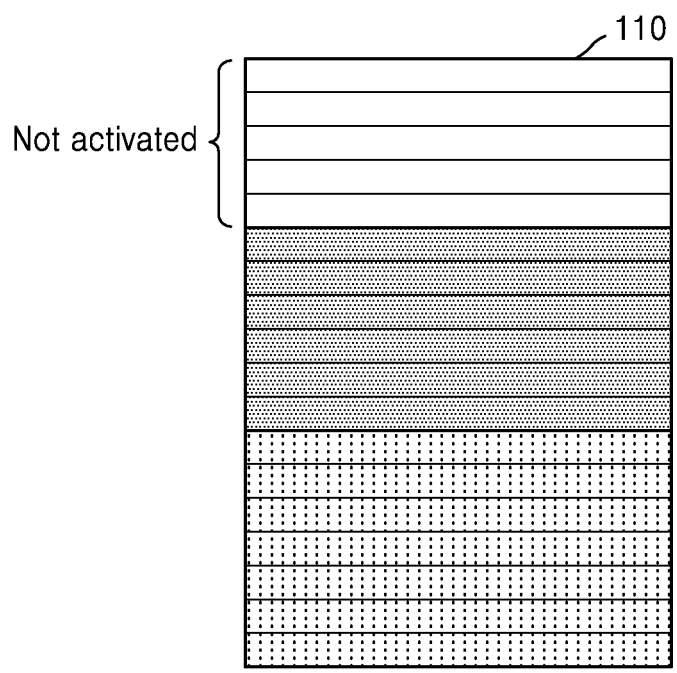
Figure 9C:
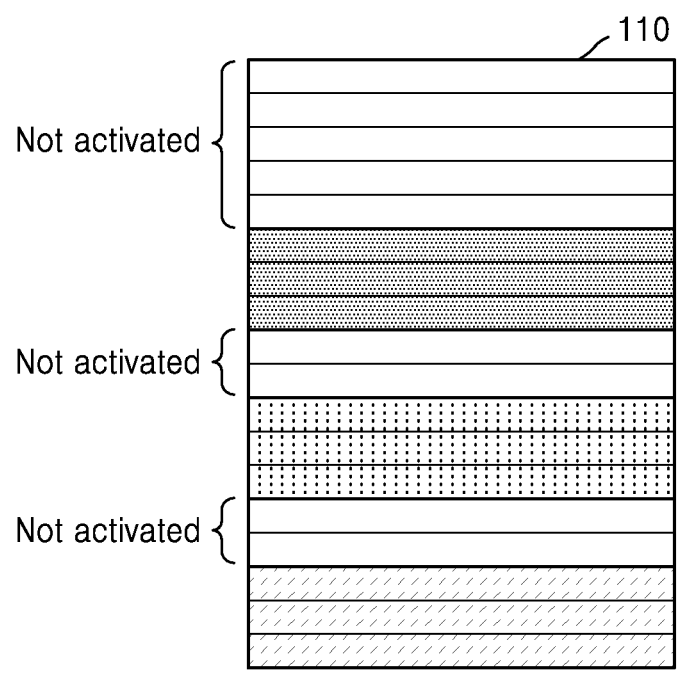

FIGS. 9A, 9B, and 9C are views for explaining various types of biosignal electrodes formed on the first electrode array 110 when the touch panel apparatus 100 is in the measuring mode, according to another exemplary embodiment.

The controller 130 of the touch panel apparatus 100 combines the electrodes included in the first electrode array 110 to form the biosignal electrodes measuring the biosignals when the touch panel apparatus 100 is in the measuring mode. The controller 130 of the touch panel apparatus 100 may adjust sizes and locations of the biosignal electrodes.

In consideration of shapes of the biosignal electrodes of FIGS. 9A to 9C, electrodes disposed in a location corresponding to the first area of the second electrode array 120 are inactivated, and thus, it is understood that the electrodes are not used as the biosignal electrodes. Because the first area of the second electrode array 120 is not connected to ground, the electrodes disposed in the location corresponding to the first area of the second electrode array 120 do not perform shielding.

FIG. 9A shows when the touch panel apparatus 100 is in the measuring mode, all electrodes disposed in the location corresponding to the second area of the second electrode array 120 among the electrodes included in the first electrode array 110 are activated, and one biosignal electrode is formed.

FIG. 9B shows when the touch panel apparatus 100 is in the measuring mode, all electrodes disposed in the location corresponding to the second area of the second electrode array 120 among the electrodes included in the first electrode array 110 are activated, and two biosignal electrodes are formed.

FIG. 9C shows when the touch panel apparatus 100 is in the measuring mode, some electrodes disposed in the location corresponding to the second area of the second electrode array 120 among the electrodes included in the first electrode array 110 are activated, and three biosignal electrodes are formed by being separate from each other by inactivated electrodes.

When the touch panel apparatus 100 is in the measuring mode, shapes of the biosignal electrodes formed in the first electrode array 110 are not limited thereto.

The touch panel apparatus 100 may measure bio-impedance signals. Information concerning body tissues may be identified by using the bio-impedance signals. For example, bio-impedance signals for measuring body fat may be measured by using the biosignal electrodes generated when the touch panel apparatus 100 is in the measuring mode. When the touch panel apparatus 100 is in the measuring mode, the driving power is applied to the first area of the second electrode array 120, and the second area of the second electrode array 120 is connected to ground. After two biosignal electrodes are formed in locations of the first electrode array 110 corresponding to the second area of the second electrode array 120, a body part of the user comes in contact with the two biosignal electrodes, and the bio-impedance signals may be obtained. An impedance of the body part placed in contact with the biosignal electrodes may be obtained by using voltage values respectively measured from the biosignal electrodes formed in the first electrode array 110. As the obtained impedance is converted into an amount of body fat, the body fat may be measured.

Figure 10A:
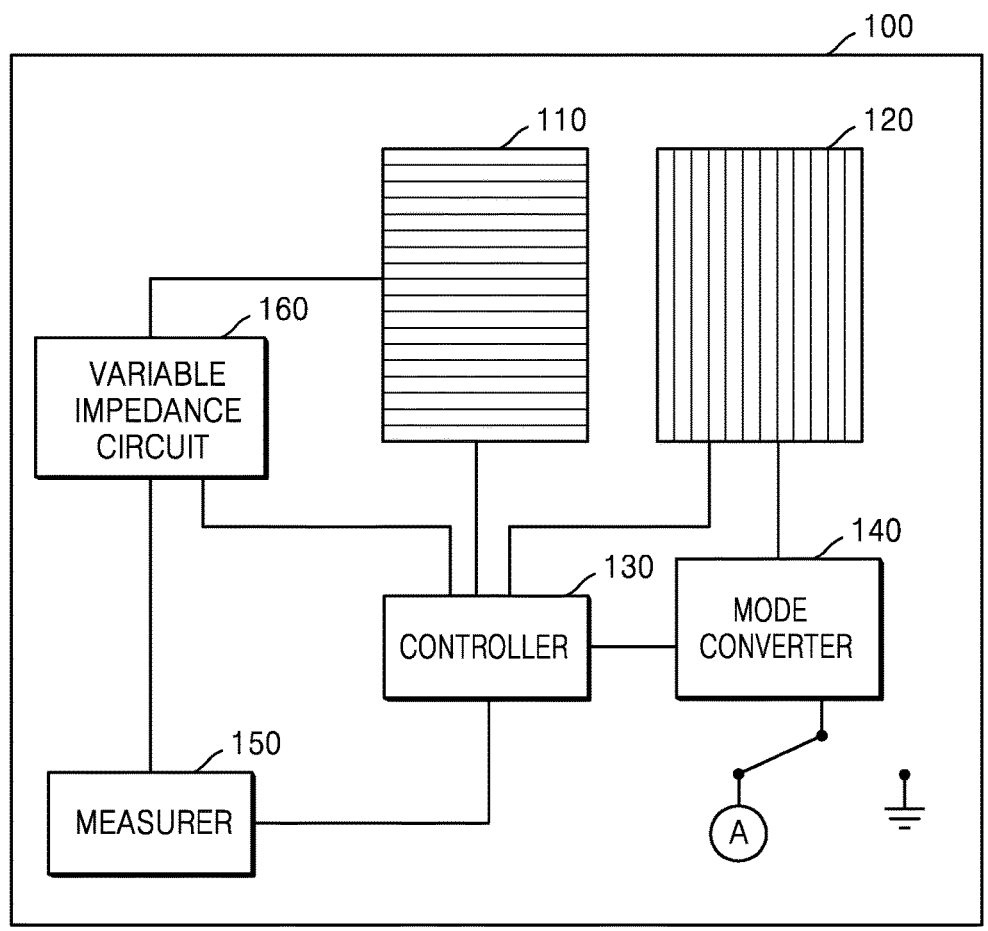
FIGS. 10A and 10B are block diagrams of structures and operations of a touch panel apparatus when operation modes of the touch panel apparatus are a manipulation mode and a measuring mode, according to another exemplary embodiment.
Figure 10B:
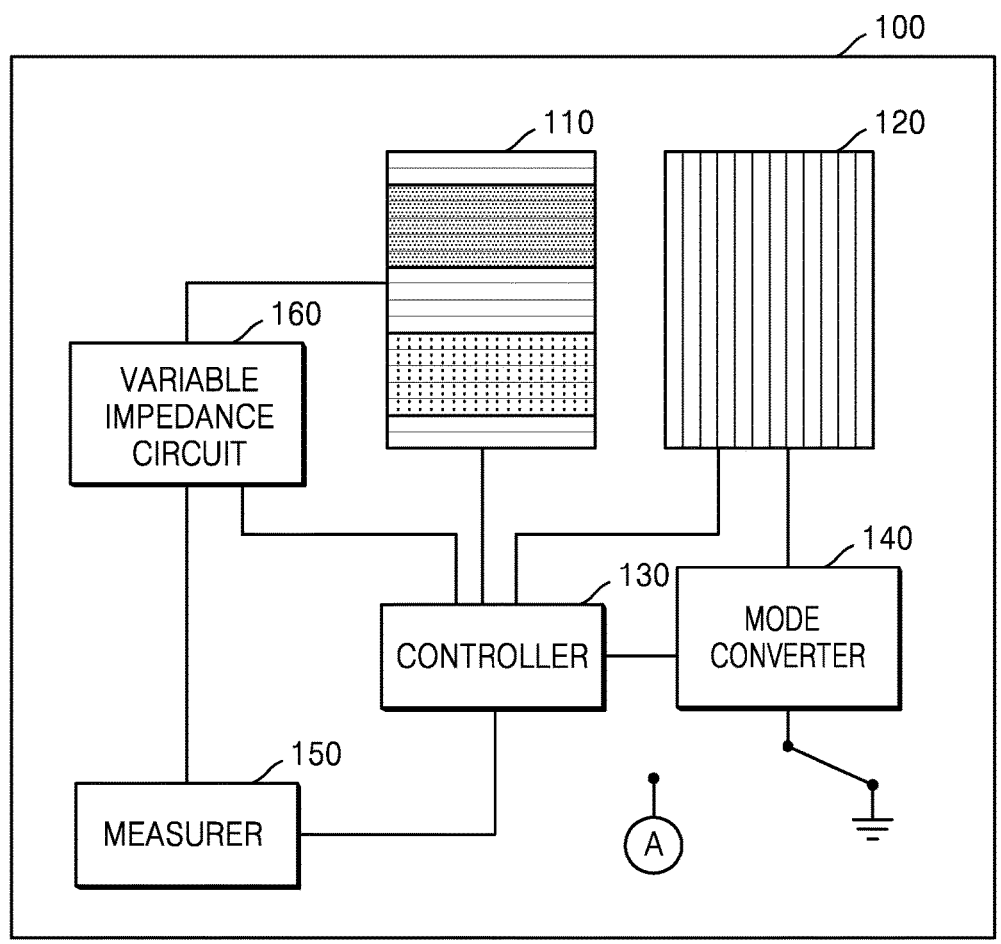

FIGS. 10A and 10B are block diagrams of structures and operations of the touch panel apparatus 100 when operation modes of the touch panel apparatus 100 are a manipulation mode and a measuring mode, according to another exemplary embodiment. It may be understood by one of ordinary skill in the art that general-purpose components, other than the components illustrated in FIGS. 10A and 10B, may be further included.

When the touch panel apparatus 100 of FIGS. 10A and 10B is compared with the touch panel apparatus 100 of FIGS. 2A and 2B, the touch panel apparatus 100 of the FIGS. 10A and 10B further includes a variable impedance circuit 160. Descriptions regarding the components of the touch panel apparatus 100 that have been provided with reference to FIGS. 2A and 2B will not be repeated.

The variable impedance circuit 160 may be connected to the first electrode array 110. The variable impedance circuit 160 may include a variable resistance. The controller 130 of the touch panel apparatus 100 may adjust the variable impedance of the variable impedance circuit 160 to adjust an input impedance of the first electrode array 110 in the measuring mode to be larger than an input impedance of the first electrode array 110 in the manipulation mode so that the first electrode array 110 may detect biosignals having a small amplitude. When the touch panel apparatus 100 is in the measuring mode, if the input impedance of the first electrode array 110 is increased, a difference between the input impedance of the first electrode array 110 and the impedance of the body part placed in contact with the touch panel apparatus 100 becomes large, and thus, the biosignals are transmitted to the first electrode array 110. As leakage of the biosignals is prevented, the biosignals having a small amplitude may be detected. An input impedance of the biosignal electrodes generated when the touch panel apparatus 100 is in the measuring mode may be increased to accurately measure bioelectric signals such as ECG signals. The controller 130 of the touch panel apparatus 100 may control the variable impedance circuit 160 based on the bioelectric signals measured by the measurer 150.

Figure 11A:
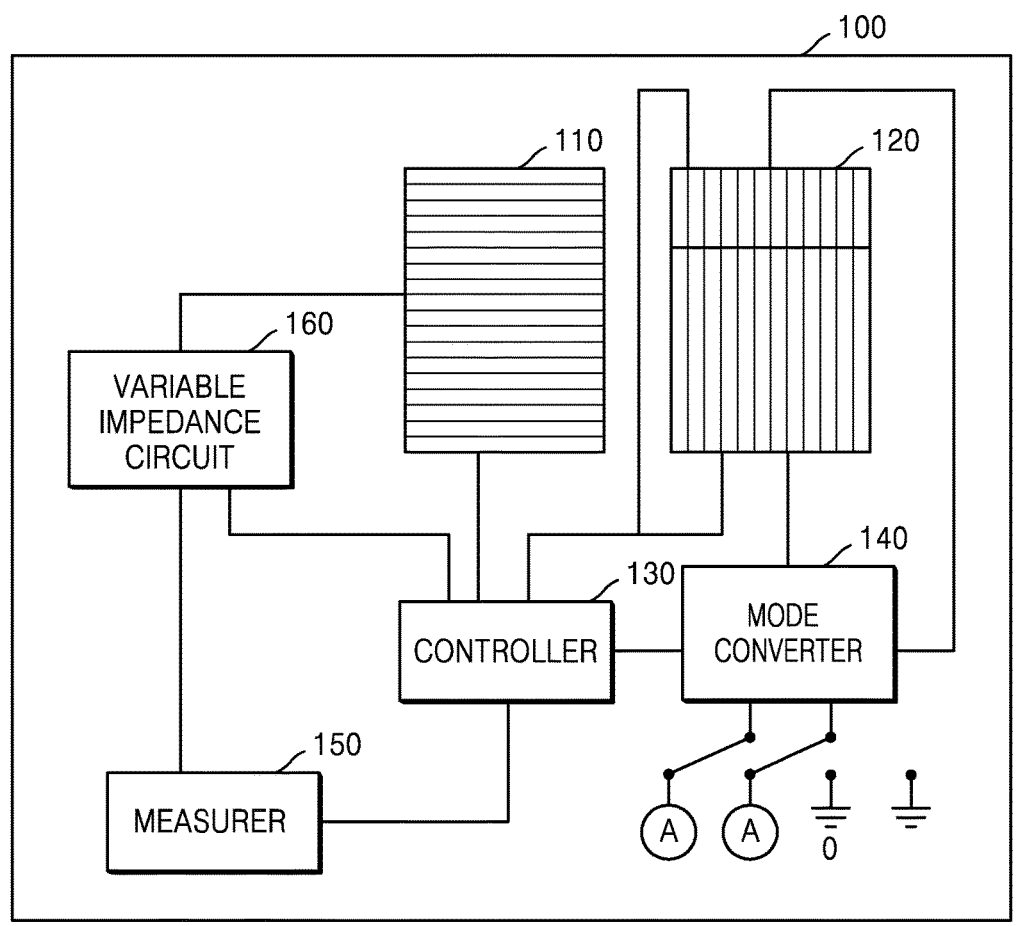
FIGS. 11A and 11B are block diagrams of structures and operations of a touch panel apparatus when operation modes of the touch panel apparatus are a manipulation mode and a measuring mode, according to another exemplary embodiment.
Figure 11B:
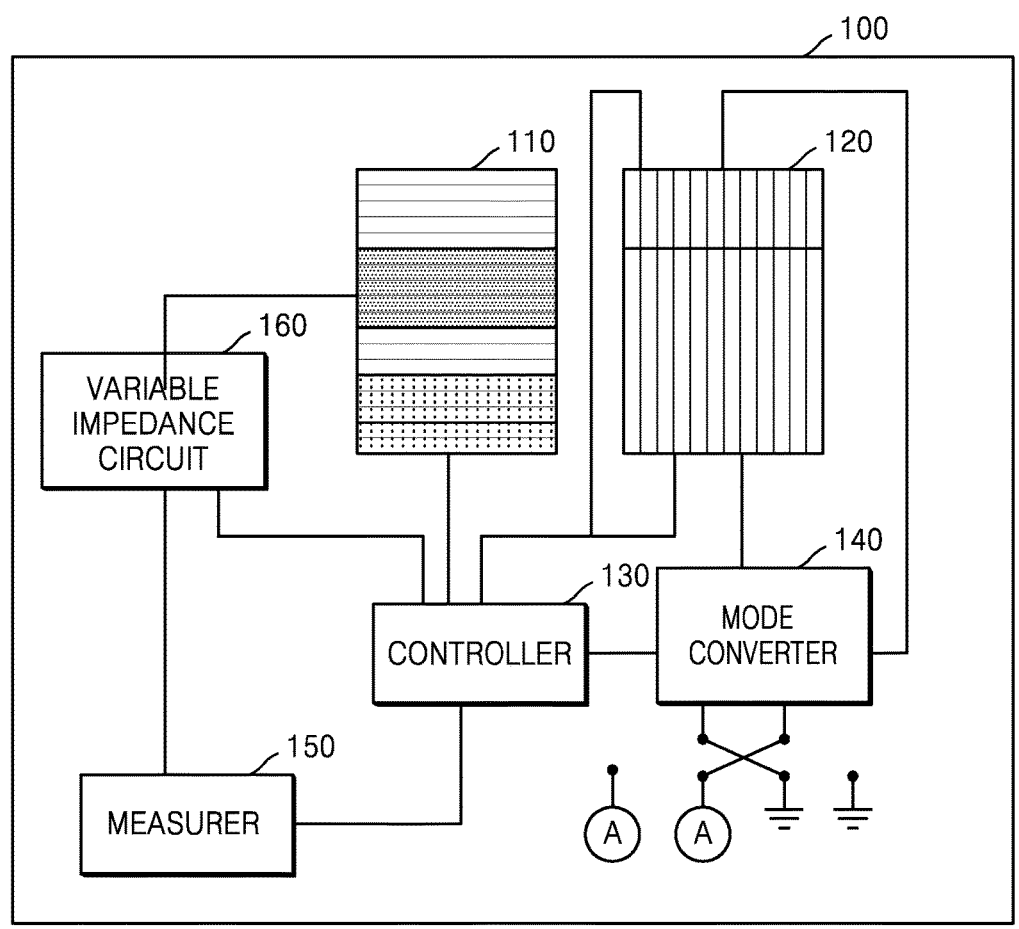

FIGS. 11A and 11B are block diagrams of structures and operations of the touch panel apparatus 110 when operation modes of the touch panel apparatus 100 are a manipulation mode and a measuring mode, according to another exemplary embodiment. It may be understood by one of ordinary skill in the art that general-purpose components, other than the components illustrated in FIGS. 10A and 10B, may be further included.

When the touch panel apparatus 100 of FIGS. 11A and 11B is compared with the touch panel apparatus 100 of FIGS. 6A and 6B, the touch panel apparatus 100 of the FIGS. 10A and 10B further includes the variable impedance circuit 160. Descriptions regarding the components of the touch panel apparatus 100 that have been provided with reference to FIGS. 6A and 6B will not be repeated.

The variable impedance circuit 160 may be connected to the first electrode array 110. The variable impedance circuit 160 may include a variable resistance. The controller 130 of the touch panel apparatus 100 may adjust the variable impedance of the variable impedance circuit 160 to adjust the input impedance of the first electrode array 110 in the measuring mode to be larger than the input impedance of the first electrode array 110 in the manipulation mode so that the first electrode array 110 may detect biosignals having a small amplitude. The controller 130 of the touch panel apparatus 100 may control the variable impedance circuit 160 based on the bioelectric signals measured by the measurer 150.

Figure 12:
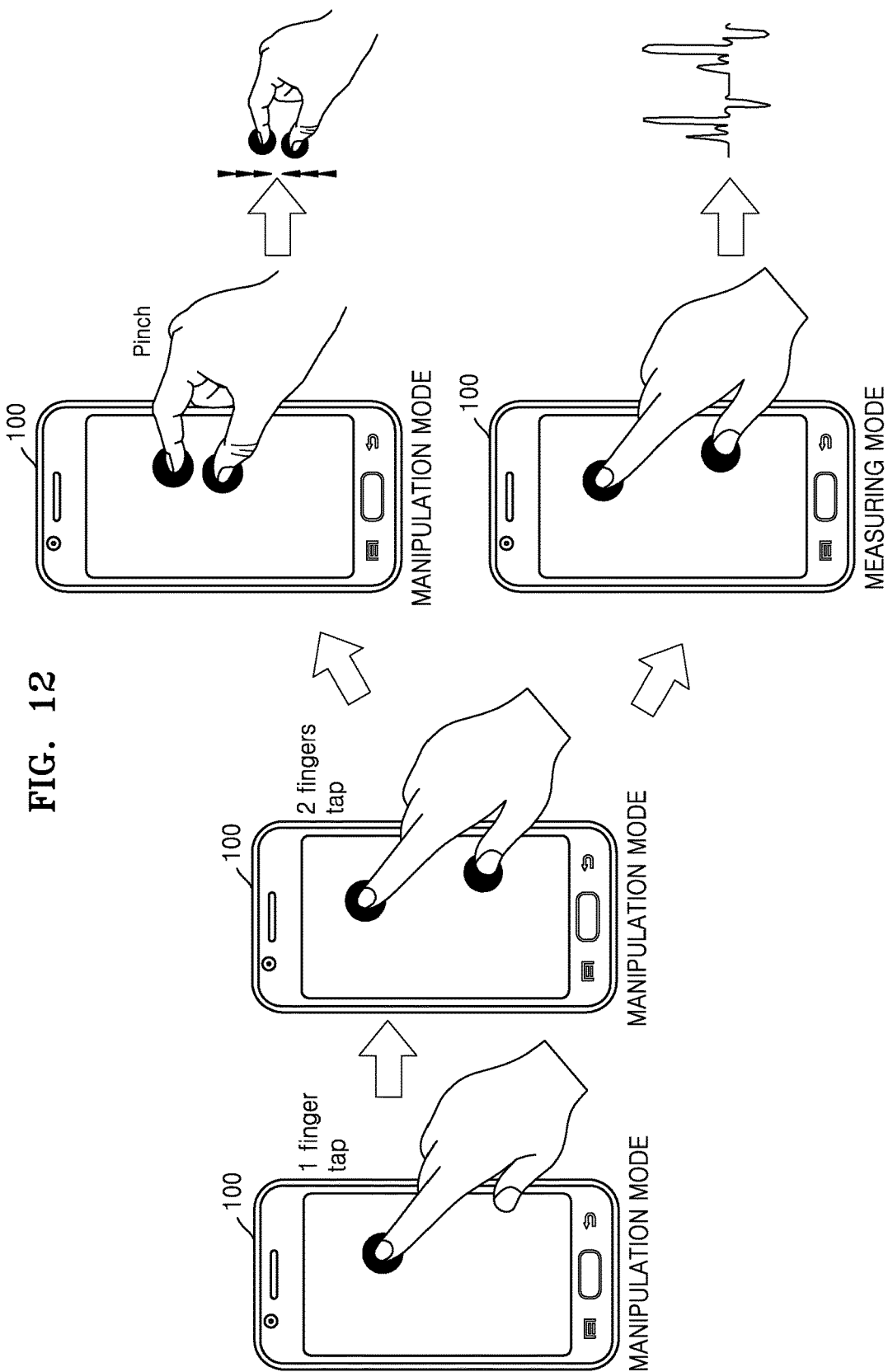
FIG. 12 is a view for explaining a method of detecting a touch input signal when an operation mode of a touch panel apparatus is converted from a manipulation mode to a measuring mode, according to an exemplary embodiment.

FIG. 12 is a view for explaining a method of detecting a touch input signal when an operation mode of the touch panel apparatus 100 is converted from a manipulation mode to a measuring mode, according to an exemplary embodiment.

The user touches the screen of the touch panel apparatus 100 with a body part and may manipulate the screen. As shown in FIG. 12, the user taps the screen of the touch panel apparatus 100 with a fingertip to manipulate the screen.

In the manipulation mode, when the user uses two fingers to tap the screen of the touch panel apparatus 100, the touch panel apparatus 100 may determine the operation mode of the touch panel apparatus 100 as either the manipulation mode or the measuring mode. For example, according to whether locations or patterns of detected touch input signals are changed, the operation mode of the touch panel apparatus 100 may be automatically determined. If the locations or patterns of detected touch input signals are changed, the operation mode of the touch panel apparatus 100 may be determined as the manipulation mode because it is determined that the touch input signals of the user are for manipulating the screen. If the locations or patterns of detected touch input signals are not changed, the operation mode of the touch panel apparatus 100 may be determined as the measuring mode because it is determined that the touch input signals of the user are for measuring the biosignals.

When the locations or patterns of detected touch input signals, which are measured in the measuring mode, are changed, the operation mode of the touch panel apparatus 100 may be automatically converted to the manipulation mode. In detail, the controller 130 of the touch panel apparatus 100 determines the operation mode of the touch panel apparatus 100 as the manipulation mode, and may control the mode converter 140, if the locations or patterns of the touch input signals detected in the measuring mode are changed.

As the operation mode of the touch panel apparatus 100 is automatically determined by monitoring the touch input signals of the user, the user may naturally measure the biosignals without performing any intentional actions for measuring the biosignals.

Figure 13:
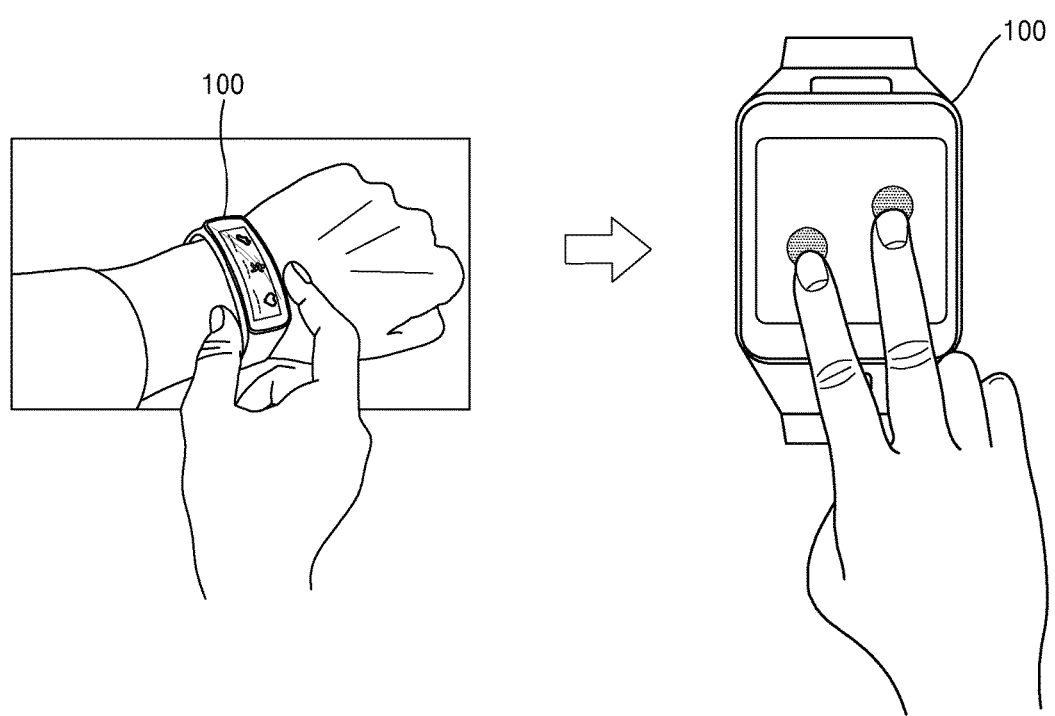
FIG. 13 is a view for explaining a method of detecting a touch input signal when an operation mode of a touch panel apparatus is converted from a manipulation mode to a measuring mode, according to another exemplary embodiment.

FIG. 13 is a view for explaining a method of detecting a touch input signal when an operation mode of touch panel apparatus 100 is converted from a manipulation mode to a measuring mode, according to another exemplary embodiment.

As shown in FIG. 13, the touch panel apparatus 100 may be a wearable device such as a smart watch. The user presses a push button and may convert the operation mode of the touch panel apparatus 100 to the measuring mode measuring the biosignals. As the operation mode is converted to the measuring mode, a user interface for measuring the biosignals is displayed on the screen of the touch panel apparatus 100, and the user may measure the biosignals by touching the user interface with a body part. In this case, the user interface displayed on the screen of the touch panel apparatus 100 may be displayed such that the user interface may correspond to locations of the biosignal electrodes formed in the first electrode array 110 of the touch panel apparatus 100.

Figure 14:
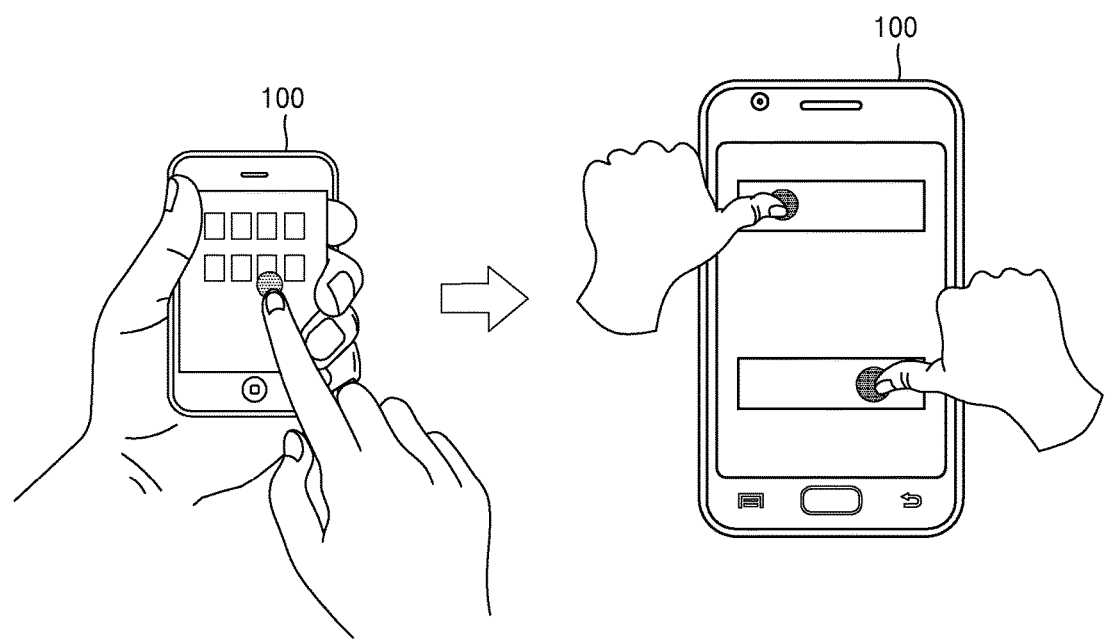
FIG. 14 is a view for explaining a method of detecting a touch input signal when an operation mode of a touch panel apparatus is converted from a manipulation mode to a measuring mode, according to another exemplary embodiment.

FIG. 14 is a view for explaining a method of detecting a touch input signal when an operation mode of the touch panel apparatus 100 is converted from a manipulation mode to a measuring mode, according to another exemplary embodiment.

As shown in FIG. 14, the touch panel apparatus 100 may be a mobile terminal such as a smart phone. The user selects an application regarding the measurement of the biosignals from applications installed in the touch panel apparatus 100, and may convert the operation mode of the touch panel apparatus 100 to the measuring mode measuring the biosignals. As the operation mode is converted to the measuring mode, the user interface for measuring the biosignals is displayed on the screen of the touch panel apparatus 100, and the user may measure the biosignals by touching the user interface with a body part. In this case, the user interface displayed on the screen of the touch panel apparatus 100 may be displayed such that the user interface may correspond to locations of the biosignal electrodes formed in the first electrode array 110 of the touch panel apparatus 100.

As shown in FIGS. 13 and 14, the touch panel apparatus 100 receives a touch input signal, which requests a mode conversion, from the user, and may determine the operation mode of the touch panel apparatus 100 according to the received touch input signal. For example, if the biosignals are intentionally measured every day at a fixed time, the user sends a request for converting the operation mode to the measuring mode to measure the biosignals.

Figure 15:
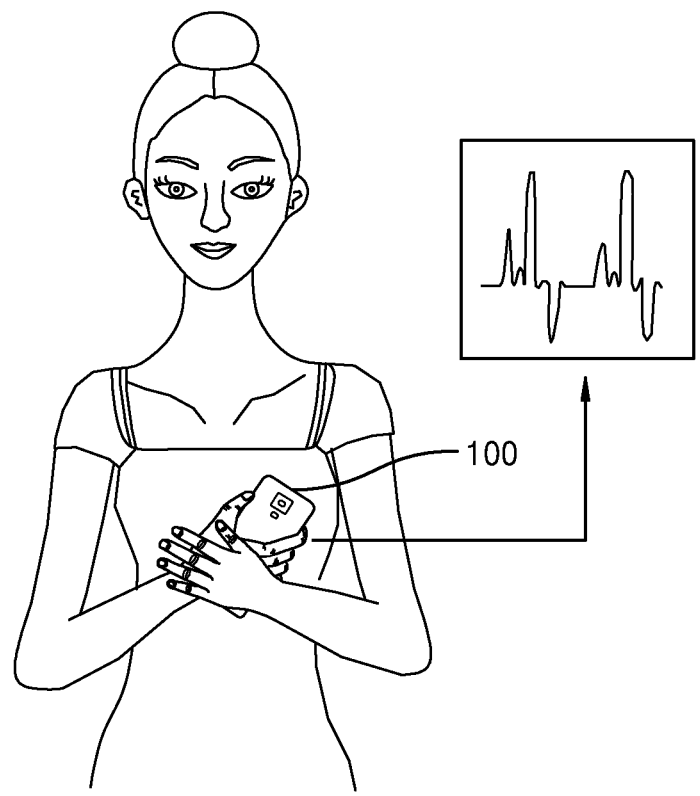
FIG. 15 is a view for explaining a method of detecting a touch input signal when a touch panel apparatus is in a measuring mode, according to an exemplary embodiment.

FIG. 15 is a view for explaining a method of detecting a touch input signal when the touch panel apparatus 100 is in a measuring mode, according to an exemplary embodiment.

The user may convert the operation mode of the touch panel apparatus 100 to the measuring mode or may touch the screen of the touch panel apparatus 100 with a body part while the touch panel apparatus 100 is on so that the biosignals such as ECG signals may be measured. For example, areas adjacent to the heart of the user may be placed in contact with the screen of the touch panel apparatus 100. Accordingly, the touch panel apparatus 100 is in the measuring mode and may measure the biosignals.

According to a thickness of clothes of the user, etc., a variable impedance connected to the first electrode array 110 of the touch panel apparatus 100 may be automatically adjusted.

Figure 16:
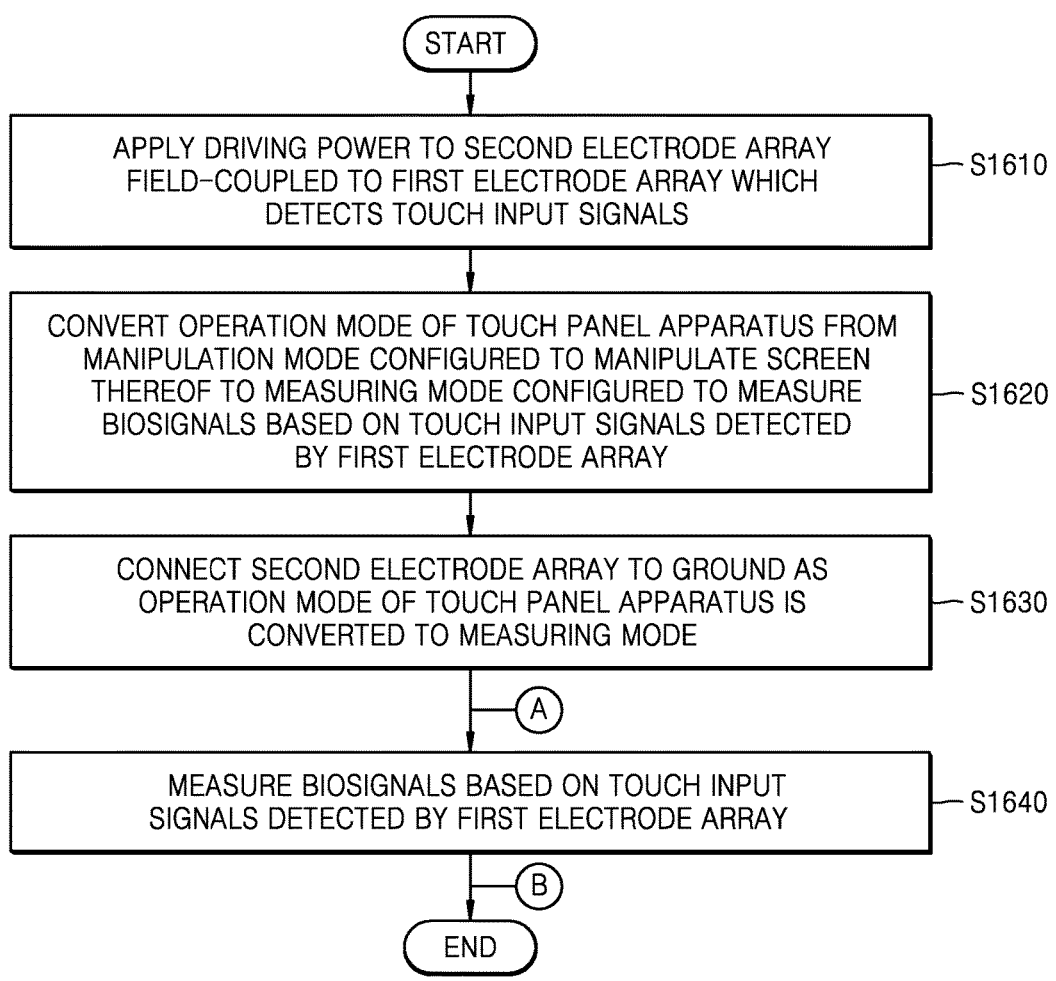
FIG. 16 is a flowchart of a method of measuring biosignals by using a touch panel apparatus, according to an exemplary embodiment.

FIG. 16 is a flowchart of a method of measuring biosignals by using the touch panel apparatus 100, according to an exemplary embodiment. Although some descriptions regarding the method are omitted, the above descriptions regarding the touch panel apparatus 100 may be applied to descriptions regarding the method.

In operation S1610, the touch panel apparatus 100 applies driving power to the second electrode array 120 field-coupled to the first electrode array 110, which detects touch input signals.

In operation S1620, the touch panel apparatus 100 converts the operation mode of the touch panel apparatus 100 from the manipulation mode configured to manipulate the screen thereof to the measuring mode configured to measure the biosignals, based on the touch input signals detected by the first electrode array 110. For example, according to locations or patterns of the detected touch input signals, the touch panel apparatus 100 may automatically convert the operation mode. As another example, according to a touch input signal requesting a mode conversion, the touch panel apparatus 100 may convert the operation mode.

In operation S1630, as the operation mode of the touch panel apparatus 100 is converted to the measuring mode, the touch panel apparatus 100 connects the second electrode array 120 to ground. Also, as the operation mode is converted to the measuring mode, the touch panel apparatus 100 may adjust an input impedance of the first electrode array 110 in the measuring mode to be larger than an input impedance of the first electrode array 110 in the manipulation mode.

In operation S1640, the touch panel apparatus 100 measures the biosignals based on the touch input signals detected by the first electrode array 110. The touch panel apparatus 100 may measure sizes of the biosignals instead of measuring at least one of the locations and patterns of the detected touch input signals.

Figure 17:
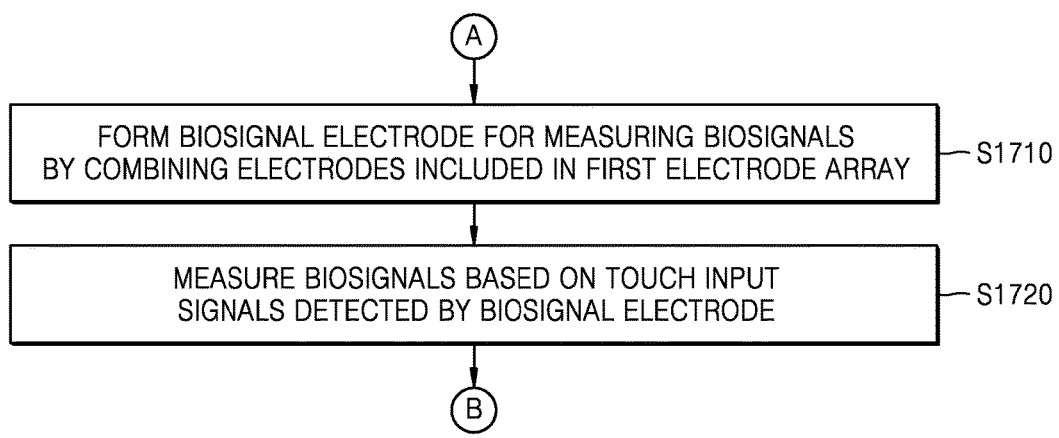
FIG. 17 is a detailed flowchart of an operation of measuring biosignals of the method of FIG. 16.

FIG. 17 is a detailed flowchart of an operation of measuring biosignals of the method of FIG. 16.

In operation S1710, in the measuring mode, the touch panel apparatus 100 forms at least one biosignal electrode for measuring the biosignals by combining the electrodes included in the first electrode array 110. As biosignal electrodes are formed in locations of the first electrode array 110 corresponding to the second electrode array 120 connected to ground, the biosignal electrodes may be shielded by the second electrode array 120. The touch panel apparatus 100 may form the biosignal electrodes by adjusting the sizes and locations of the biosignal electrodes.

In operation S1720, the touch panel apparatus 100 measures the biosignals based on the touch input signals detected by the biosignal electrode.

Figure 18:
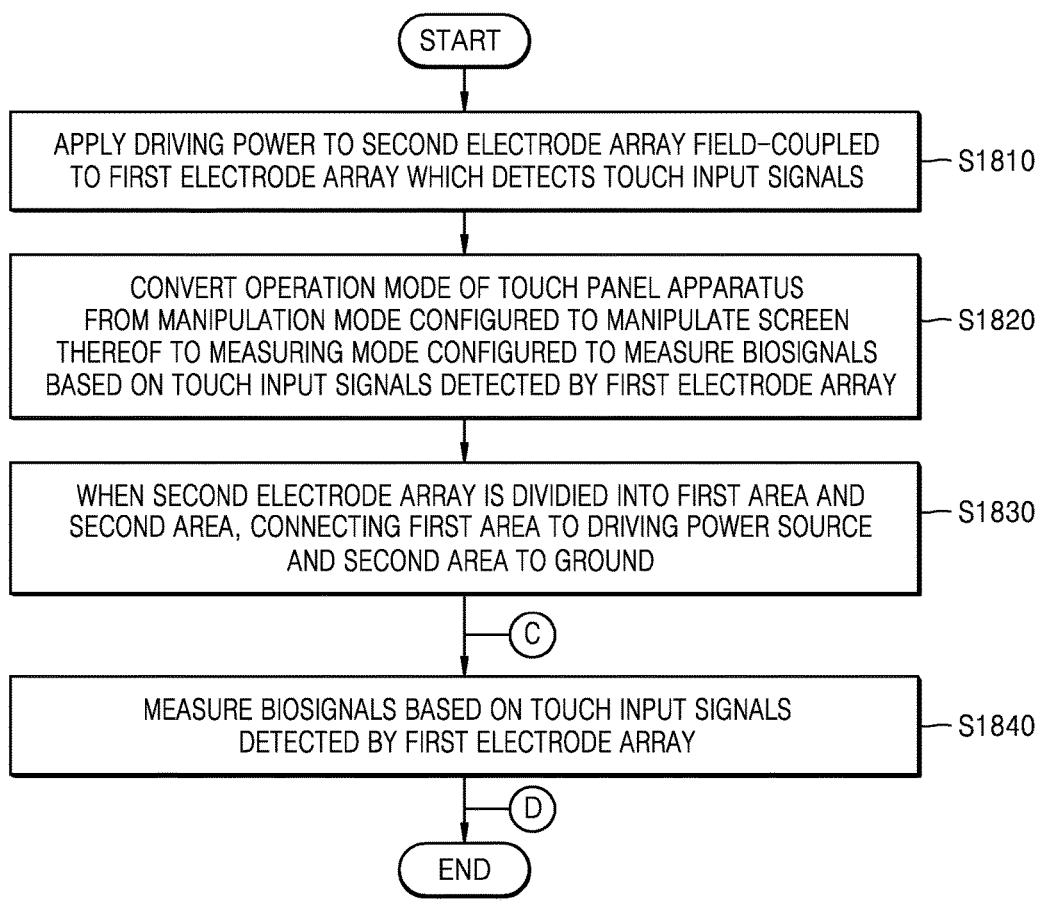
FIG. 18 is a flowchart of a method of measuring biosignals by using a touch panel apparatus, according to another exemplary embodiment.

FIG. 18 is a flowchart of a method of measuring biosignals by using the touch panel apparatus 100, according to another exemplary embodiment. Although some descriptions regarding the method are omitted, the above descriptions regarding the touch panel apparatus 100 may be applied to descriptions regarding the method of measuring biosignals by using the touch panel apparatus 100.

In operation S1810, the touch panel apparatus 100 applies the driving power to the second electrode array 120 field-coupled to the first electrode array 110, which detects the touch input signals.

In operation S1820, the touch panel apparatus 100 converts the operation mode of the touch panel apparatus 100 from the manipulation mode configured to manipulate the screen thereof to the measuring mode configured to measure the biosignals, based on the touch input signals detected by the first electrode array 110. For example, according to the locations or patterns of the detected touch input signals, the touch panel apparatus 100 may automatically convert the operation mode. As another example, according to a touch input signal requesting a mode conversion, the touch panel apparatus 100 may convert the operation mode.

In operation S1830, when the second electrode array 120 is divided into the first area and the second area, the touch panel apparatus 100 connects the first area to the driving power source and the second area to ground. Also, as the operation mode of the touch panel apparatus 100 is converted to the measuring mode, the touch panel apparatus 100 may adjust the input impedance of the first electrode array 110 in the measuring mode to be larger than the input impedance of the first electrode array 110 in the manipulation mode.

In operation S1840, the touch panel apparatus 100 measures the biosignals based on the touch input signals detected by the first electrode array 110. The touch panel apparatus 100 may measure the sizes of the biosignals instead of measuring at least one of the locations and patterns of the detected touch input signals.

Figure 19:
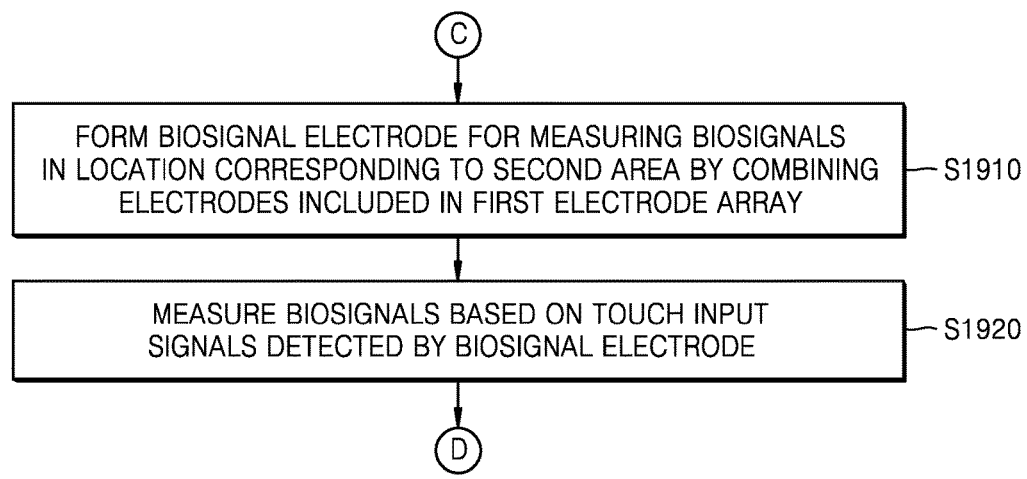
FIG. 19 is a detailed flowchart of an operation of measuring biosignals of the method of FIG. 18.

FIG. 19 is a detailed flowchart of an operation of measuring biosignals of the method of FIG. 18.

In operation S1910, the touch panel apparatus 100 forms at least one biosignal electrode for measuring the biosignals in at least one location corresponding to the second area by combining the electrodes included in the first electrode array 110. As biosignal electrodes are formed in the locations corresponding to the second area, the biosignal electrodes may be shielded by the second area of the second electrode array 120. The touch panel apparatus 100 adjusts the sizes and locations of the biosignal electrodes such that the biosignal electrodes may be formed.

In operation S1920, the touch panel apparatus 100 measures the biosignals based on the touch input signals detected by the biosignal electrode.

While not restricted thereto, an exemplary embodiment can be embodied as computer-readable code on a computer-readable recording medium. For example, a control program that controls the above-described operations may be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units can include circuitry, a processor, a microprocessor, etc., and may execute a computer program stored in a computer-readable medium.

The foregoing exemplary embodiments and advantages are examples and are not to be construed as limiting. The present teaching can be readily applied to other types of apparatuses. Also, the description of exemplary embodiments is intended to be illustrative, and not to limit the scope of the claims, and many alternatives, modifications, and variations will be apparent to those skilled in the art.

What is claimed is:

1. A touch panel apparatus for measuring biosignals, the touch panel apparatus comprising:
   a screen;
   a first electrode array on which the screen is disposed, the first electrode array comprising reception electrodes configured to detect a touch input directly on at least one location of the screen;
   a second electrode array comprising driving electrodes configured to be coupled to the first electrode array, based on a driving power, the first electrode array and the second electrode array forming a stack structure;
   a controller configured to:
      determine an operation mode of the touch panel apparatus as a manipulation mode configured to manipulate the screen, in response to the touch input being detected directly on the at least one location of the screen and then detected to move within a period of time; and
      determine the operation mode as a measuring mode configured to measure the biosignals, in response to the touch input being detected to be held for the period of time directly on the at least one location of the screen; and
   a mode converter configured to:
      connect the second electrode array to a source of the driving power, in response to the operation mode being determined as the manipulation mode; and
      connect all of the driving electrodes comprised in an entire portion of the second electrode array to ground, in response to the operation mode being determined as the measuring mode.

2. The touch panel apparatus of claim 1, wherein the controller is further configured to activate the reception electrodes comprised in the first electrode array to form a biosignal electrode configured to measure the biosignals, in response to the operation mode being determined as the measuring mode.

3. The touch panel apparatus of claim 2, wherein the controller is further configured to adjust a size and a location of the biosignal electrode by deactivating one or more of the reception electrodes activated in the first electrode array.

4. The touch panel apparatus of claim 1, further comprising a variable impedance circuit connected to the first electrode array,
   wherein the controller is further configured to adjust a first impedance of the variable impedance circuit to adjust an input impedance of the first electrode array to be larger in the measuring mode than in the manipulation mode, in response to the operation mode being determined as the measuring mode.

5. The touch panel apparatus of claim 1, wherein, based on the second electrode array being divided into a first area and a second area, the mode converter is further configured to connect the first area to the source of the driving power, and connect the second area to ground, in response to the operation mode being determined as the measuring mode.

6. The touch panel apparatus of claim 5, wherein the controller is further configured to, in response to the measuring mode being determined as the measuring mode:
   activate a first portion of the reception electrodes comprised in the first electrode array, the first portion being in a first location corresponding to the second area of the second electrode array, to form a biosignal electrode configured to measure the biosignals; and
   deactivate a remaining portion of the reception electrodes, the remaining portion being in a second location corresponding to the first area of the second electrode array.

7. The touch panel apparatus of claim 1, further comprising a measurer configured to:
   measure any one or any combination of locations and patterns of the touch input that is detected, in response to the operation mode being determined as the manipulation mode; and
   measure sizes of the biosignals, based on the touch input that is detected, in response to the operation mode being determined as the measuring mode.

8. The touch panel apparatus of claim 1, wherein the controller is further configured to determine the operation mode as the manipulation mode or the measuring mode, based on any one or any combination of locations and patterns of the touch input that is detected.

9. The touch panel apparatus of claim 8, wherein the controller is further configured to, based on any one or any combination of the locations and patterns of the touch input that is detected being changed, determine the operation mode as the manipulation mode.

10. The touch panel apparatus of claim 1, wherein the controller is further configured to determine the operation mode as the manipulation mode or the measuring mode, based on the touch input that is detected requesting a conversion of the operation mode.

11. A method of measuring biosignals by using a touch panel apparatus, the method comprising:
   applying a driving power to a second electrode array comprising driving electrodes, to couple the second electrode array to a first electrode array comprising reception electrodes detecting a touch input directly on at least one location of a screen of the touch panel apparatus, the screen being disposed on the first electrode array, and the first electrode array and the second electrode array forming a stack structure;
   determining an operation mode of the touch panel apparatus as a manipulation mode configured to manipulate the screen, in response to the touch input being detected directly on the at least one location of the screen and then detected to move within a period of time;
   determining the operation mode as a measuring mode configured to measure the biosignals, in response to the touch input being detected to be held for the period of time directly on the at least one location of the screen;
   connecting the second electrode array to a source of the driving power, in response to the operation mode being determined as the manipulation mode; and
   connecting all of the driving electrodes comprised in an entire portion of the second electrode array to ground, and measuring the biosignals, based on the touch input that is detected, in response to the operation mode being determined as the measuring mode.

12. The method of claim 11, further comprising activating the reception electrodes comprised in the first electrode array to form a biosignal electrode measuring the biosignals, in response to the operation mode being determine as the measuring mode,
   wherein the measuring comprises measuring the biosignals, based on the touch input detected by the biosignal electrode that is formed.

13. The method of claim 12, further comprising adjusting a size and a location of the biosignal electrode by deactivating one or more of the reception electrodes activated in the first electrode array.

14. The method of claim 11, further comprising adjusting an input impedance of the first electrode array to be larger in the measuring mode than in the manipulation mode, in response to the operation mode being determined as the measuring mode, wherein the measuring comprises measuring the biosignals, based on the touch input detected by the first electrode array having the input impedance that is adjusted.

15. The method of claim 11, wherein the connecting the second electrode array comprises, based on the second electrode array being divided into a first area and a second area, connecting the first area to the source of the driving power, and connecting the second area to ground, in response to the operation mode being determined as the measuring mode.

16. The method of claim 15, further comprising, in response to the operation mode being determined as the measuring mode:

activating a first portion of the reception electrodes comprised in the first electrode array, the first portion being in a first location corresponding to the second area of the second electrode array, to form a biosignal electrode measuring the biosignals; and deactivating a remaining portion of the reception electrodes, the remaining portion being in a second location corresponding to the first area of the second electrode array, wherein the measuring comprises measuring the biosignals, based on the touch input detected by the biosignal electrode that is formed.

17. The method of claim 11, further comprising measuring any one or any combination of locations and patterns of the touch input that is detected, in response to the operation mode being determined as the manipulation mode, wherein the measuring the biosignals comprises measuring sizes of the biosignals, based on the touch input that is detected, in response to the operation mode being determined as the measuring mode.

18. The method of claim 11, wherein the determining the operation mode as the manipulation mode comprises determining the operation mode as the manipulation mode, based on any one or any combination of locations and patterns of the touch input that is detected being changed.

19. The method of claim 11, further comprising determining the operation mode as the manipulation mode or the measuring mode, based on the touch input that is detected requesting a conversion of the operation mode.

20. A non-transitory computer-readable storage medium storing a program comprising instructions configured to cause a computer to perform the method of claim 11.

21. A touch panel apparatus comprising:

a screen;

a first electrode array on which the screen is disposed, the first electrode array comprising reception electrodes configured to detect a touch input directly on at least one location of the screen;

a second electrode array comprising driving electrodes configured to be coupled to the first electrode array, based on a driving power, the first electrode array and the second electrode array forming a stack structure;

a mode converter configured to:

connect the second electrode array to a source of the driving power, in response to the touch input being detected directly on the at least one location of the screen and then detected to move within a period of time; and connect all of the driving electrodes comprised in an entire portion of the second electrode array to ground, in response to the touch input being detected to be held for the period of time directly on the at least one location of the screen.

22. The touch panel apparatus of claim 21, further comprising a measurer configured to:

measure any one or any combination of locations and patterns of the touch input that is detected, in response to the touch input being detected and then detected to move within the period of time; and measure sizes of biosignals, based on the touch input that is detected, in response to the touch input detected and then detected to not move for the period of time.

23. The touch panel apparatus of claim 21, further comprising:

a controller configured to, in response to the touch input detected and then detected to not move for the period of time:

activate a first portion of the reception electrodes comprised in the first electrode array, to form a biosignal electrode configured to measure biosignals; and deactivate a remaining portion of the reception electrodes; and a measurer configured to measure sizes of the biosignals, based on the touch input detected by the biosignal electrode that is formed.

* * * * *